United States Patent [19]
Abe et al.

[11] Patent Number: 5,684,583
[45] Date of Patent: Nov. 4, 1997

[54] APPARATUS FOR DETECTING FOREIGN MATTER IN A FLUID

[75] Inventors: Fumihiko Abe; Ken Tsukii; Hajime Noda; Nobuyuki Shinagawa; Hiroshi Maruki; Hiroshi Hayashi; Motohiro Yamane, all of Tokyo, Japan

[73] Assignee: The Furukawa Electric Co., Ltd., Tokyo, Japan

[21] Appl. No.: 535,196

[22] PCT Filed: Jun. 23, 1995

[86] PCT No.: PCT/JP95/01265

§ 371 Date: Oct. 19, 1995

§ 102(e) Date: Oct. 19, 1995

[87] PCT Pub. No.: WO96/00381

PCT Pub. Date: Jan. 4, 1996

[30] Foreign Application Priority Data

Jun. 27, 1994 [JP] Japan .................. 6-144382
Sep. 26, 1994 [JP] Japan .................. 6-229622
Apr. 28, 1995 [JP] Japan .................. 7-106478

[51] Int. Cl.$^6$ .................................. G01N 15/02
[52] U.S. Cl. ............................ 356/335; 356/336
[58] Field of Search ...................... 356/335–343, 356/429–431, 237

[56] References Cited

U.S. PATENT DOCUMENTS

| | | | |
|---|---|---|---|
| 3,591,290 | 7/1971 | Zinner | 356/335 |
| 4,514,257 | 4/1985 | Karlsson et al. | 356/335 |
| 4,529,309 | 7/1985 | Pettersson et al. | 356/335 |
| 4,920,275 | 4/1990 | Itoh | 356/338 |
| 5,185,641 | 2/1993 | Igushi et al. | 356/336 |
| 5,325,169 | 6/1994 | Nakamoto et al. | 356/336 |

FOREIGN PATENT DOCUMENTS

| | | | |
|---|---|---|---|
| 3822310 | 1/1989 | Germany | 356/335 |
| 2-2098 | 1/1990 | Japan . | |
| 3-284927 | 12/1991 | Japan . | |
| 5-249052 | 9/1993 | Japan . | |
| 7-108580 | 4/1995 | Japan . | |

*Primary Examiner*—Hoa Q. Pham
*Attorney, Agent, or Firm*—Frishauf, Holtz, Goodman, Langer & Chick

[57] ABSTRACT

In a foreign matter detecting apparatus 1, light beams are applied to a moving plastic resin extruded from an extruder, and a foreign matter, if any, in the plastic resin is detected by transmitted light beams. First and second projectors 30a,30b of the foreign matter detecting apparatus apply a plurality of light beams with different convergence diameters to the plastic resin which is extruded and moves in a passage 18. First and second light receivers 40a,40b receive the light beams transmitted through the plastic resin, and compare their respective reception levels with a plurality of levels of light reception which are previously set corresponding to the size of the foreign matter. Based on the result of comparison, the light receivers detect the presence and size of the foreign matter involved in the plastic resin.

41 Claims, 22 Drawing Sheets

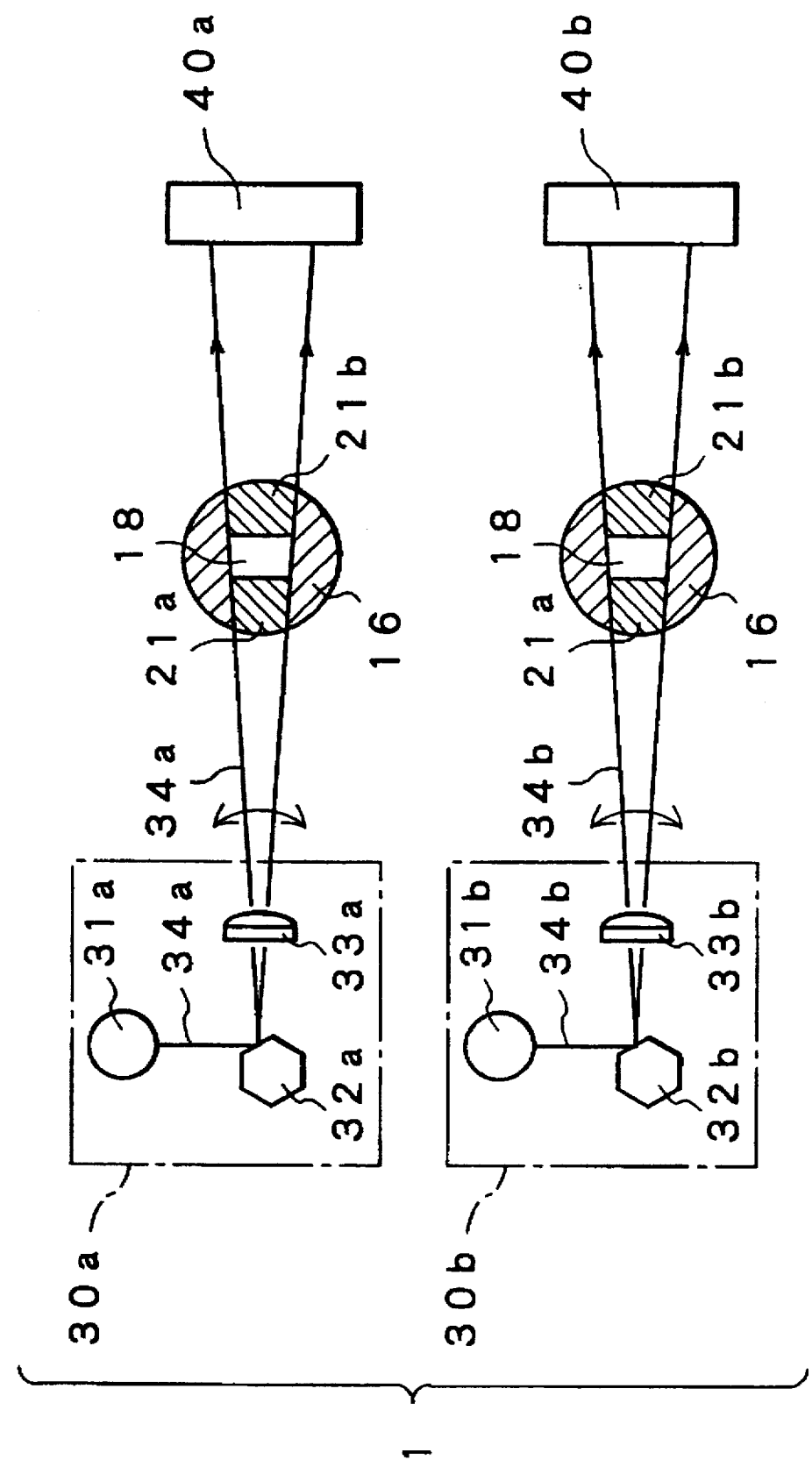

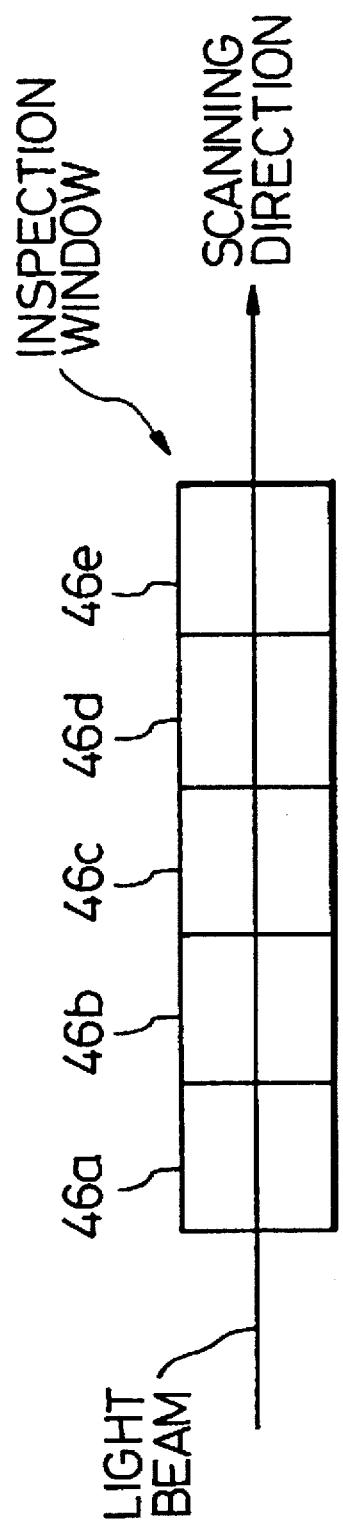

 FIG. 7A END EDGE DETECTION SIGNAL
 FIG. 7B SCANNING SIGNAL
 FIG. 7C INVERTED VERSION OF SCANNING SIGNAL
 FIG. 7D DETECTION SIGNAL
 FIG. 7E OUTPUT OF F/F
 FIG. 7F GATE OUTPUT

APPARATUS FOR DETECTING FOREIGN MATTER IN A FLUID

TECHNICAL FIELD

The present invention relates to an apparatus for detecting foreign matter, if any, in a moving fluid which transmits light, e.g., a moving molten resin which is extruded from an extruder.

BACKGROUND ART

Conventionally, high-voltage cables are used at voltages of 275 kV and 500 kV, for example. These high-voltage cables have a problem that the long-term performance of their insulating plastic covering lowers as the service voltage increases. It is known that the lowering of this performance may be caused by minute foreign matters which penetrate a plastic resin (hereinafter referred to simply as "plastic") during manufacturing processes for the high-voltage cables.

In some apparatuses for manufacturing these high-voltage cables, foreign matters are removed beforehand by means of a mesh screen provided in a passage through which an extruded insulating plastic for covering the cables flows, in order to prevent the foreign matters from penetrating the plastic. Although relatively large foreign matters can be seized by the mesh screen, however, some minute ones may possibly get through fine meshes of the screen. It is necessary, therefore, to inspect in advance the plastic extruded from a plastic extruder for the presence of minute foreign matters therein and remove them.

To attain this, some conventional plastic extruders are furnished with a foreign matter detecting apparatus, such as the one described in Unexamined Japanese Patent Publication (KOKAI) No. 3-284927 (filed Mar. 30, 1990), which is designed to detect foreign matters in a plastic formed by means of the extruder. In this foreign matter detecting apparatus, a minute foreign matter is detected by applying a constricted light beam to the plastic by means of a projector. The transmitted light beam is received by means of a light receiver, and a peak value proportional to the size of the foreign matter in the plastic is obtained from differential waveforms indicative of changes of received light quantities for the foreign matter.

In the foreign matter detecting apparatus of this type, however, the light beam is baffled entirely by a foreign matter of a size larger than its convergence diameter (convergence diameter<foreign matter size), so that the maximum peak value is exceeded. Theoretically, therefore, an accurate foreign matter size cannot be specified in accordance with the differential waveforms.

The foreign matter size may be estimated by measuring the received light quantity reduction time from a voltage waveform obtained before differentiation. This method is impractical, however, since the actual voltage waveform is canceled by noises, so that the foreign matter size can hardly be discriminated.

In the case of a minute foreign matter of a size smaller than the convergence diameter of the light beam (convergence diameter>foreign matter size), there are no differences between the received light quantities, so that even the presence of the foreign matter, not to mention its size, cannot be identified on account of noises. More specifically, in manufacturing a high-voltage cable of 500-kV service voltage, for example, the size of foreign matters which are allowed to penetrate the resin is 50 µm or less with a margin in view. A foreign matter can be detected if half the optical area is baffled. If the foreign matter detection is carried out with the convergence diameter of the light beam adjusted to 70 µm (substantially equal to the product of 50 and the square root of 2), that is, with the convergence diameter not smaller than the foreign matter size, therefore, the foreign matter can be detected within the range of 50 to 70 µm or thereabout. In consideration of the security of the cable performance and feedback to the foreign matter detecting system, however, foreign matters of 70 µm or more must be discriminated.

Foreign matters contained in a molten resin may include minute elongate ones such as fibers. These minute elongate foreign matters are limited in width and move substantially parallel to the flowing direction of the resin in the passage. Possibly, therefore, these foreign matters may get through a mesh screen for use as foreign matter seizing means which is attached to a breaker plate of the extruder.

In the foreign matter detecting apparatus, moreover, it is essential to discriminate the size of minute foreign matters in the resin, in order to guarantee the cable performance. Since the size of foreign matters which are allowed to subsist in the resin varies depending on the kind of the foreign matters, whether metallic (mainly aluminum, copper, iron, etc.) or fibrous, furthermore, the foreign matter kind should be also discriminated. Since metals and fibers are different in dielectric constant and electric conductivity, the degrees of their field concentration in an insulating plastic layer vary under the load of a high voltage, thus positively causing insulation breakdown. Accordingly, there has been a demand for the development of an apparatus which can discriminate the kind of foreign matters which are allowed to subsist in the resin, as well as the size of the foreign matter.

DISCLOSURE OF THE INVENTION

The present invention has been contrived in consideration of these circumstances, and an object of the invention is to provide an apparatus for detecting foreign matters in a fluid, in which the presence and size of a foreign matter contained in a moving fluid can be accurately detected by means of light beams with different convergence diameters.

Another object of the invention is to detect the length of a foreign matter in a fluid with high accuracy.

Still another object of the invention is to reduce the size and weight of light projectors and receivers by designing them so that light beams of different convergence diameters can be simultaneously applied to one spot.

A further object of the invention is to detect the kind of a foreign matter in a moving fluid with high accuracy.

The above objects are achieved by a foreign matter detecting apparatus according to the present invention. The foreign matter detecting apparatus applies light beams to a moving light transmitting fluid, e.g., a moving molten resin extruded from an extruder, and detects a foreign matter involved in the molten resin by means of transmitted light beams. In this apparatus, a plurality of projecting means scan the light beams with different convergence diameters in a direction at right angle with the moving direction of the fluid, and apply the light beams to the fluid. A plurality of light receiving means receive the light beams transmitted through the fluid with every scanning cycle, and sensing means detects the size of the foreign matter in the fluid in accordance with the levels of reception of the received light beams. The projecting means constitute projectors, while the light receiving means and the detecting means constitute light receivers which are arranged corresponding to the projectors, individually. In the foreign matter detecting apparatus of the invention, a plurality of light beams with different convergence diameters are applied to the fluid, and the presence and size of the foreign matter in the fluid are detected in accordance with the levels of reception of the transmitted light beams.

Preferably, in the foreign matter detecting apparatus according to the present invention, the presence of the foreign matter in the fluid is discriminated in accordance with the level of reception of the transmitted light beam, and the length of the foreign matter is discriminated in accordance with the detection time for the continuously detected foreign matter.

Preferably, moreover, the sensing means of the invention detects the size of the foreign matter by comparing a plurality of previously set light reception levels with the levels of reception of the received light beams.

Preferably, in the foreign matter detecting apparatus according to the present invention, furthermore, a scanning section for the light beams applied to the fluid is divided, and the presence and length of the foreign matter are detected with every divided scanning section.

In order to apply the light beams with different convergence diameters simultaneously to one spot, moreover, it is advisable to vary the wavelengths of the light beams and couple the light beams to be applied, in the foreign matter detecting apparatus of the invention.

Preferably, in the foreign matter detecting apparatus according to the present invention, furthermore, the presence and size of the foreign matter contained in the fluid are detected, and the levels of reception of scattered light beams from the foreign matter to which the light beams are applied are detected. The reception levels of the scattered light beams are then corrected in accordance with the size of the detected foreign matter, and the kind of the foreign matter is discriminated in accordance with variations of the corrected levels of light reception.

Preferably, the foreign matter detecting apparatus of the invention is used for the detection of foreign matter in a molten resin which is formed by means of an extruder and used to cover a high-voltage cable.

The foreign matter detecting apparatus of the invention is preferably used to detect foreign matter in a molten resin which is used for forming an insulating material for covering an extrusion-molded connecting part for crosslinked polyethylene cables or high-voltage cables.

BRIEF DESCRIPTION OF THE DRAWINGS

FIG. 3 is a diagram showing an arrangement of principal parts of the apparatus;

FIG. 5 is a diagram showing an example of a divided inspection window;

FIGS. 7A to 7F show waveforms indicative of signals at various parts shown in FIG. 6;

BEST MODE OF CARRYING OUT THE INVENTION

Apparatuses for detecting foreign matters in a fluid according to the present invention are described with reference to the accompanying drawings of FIGS. 1 through 26.

Figure 1:
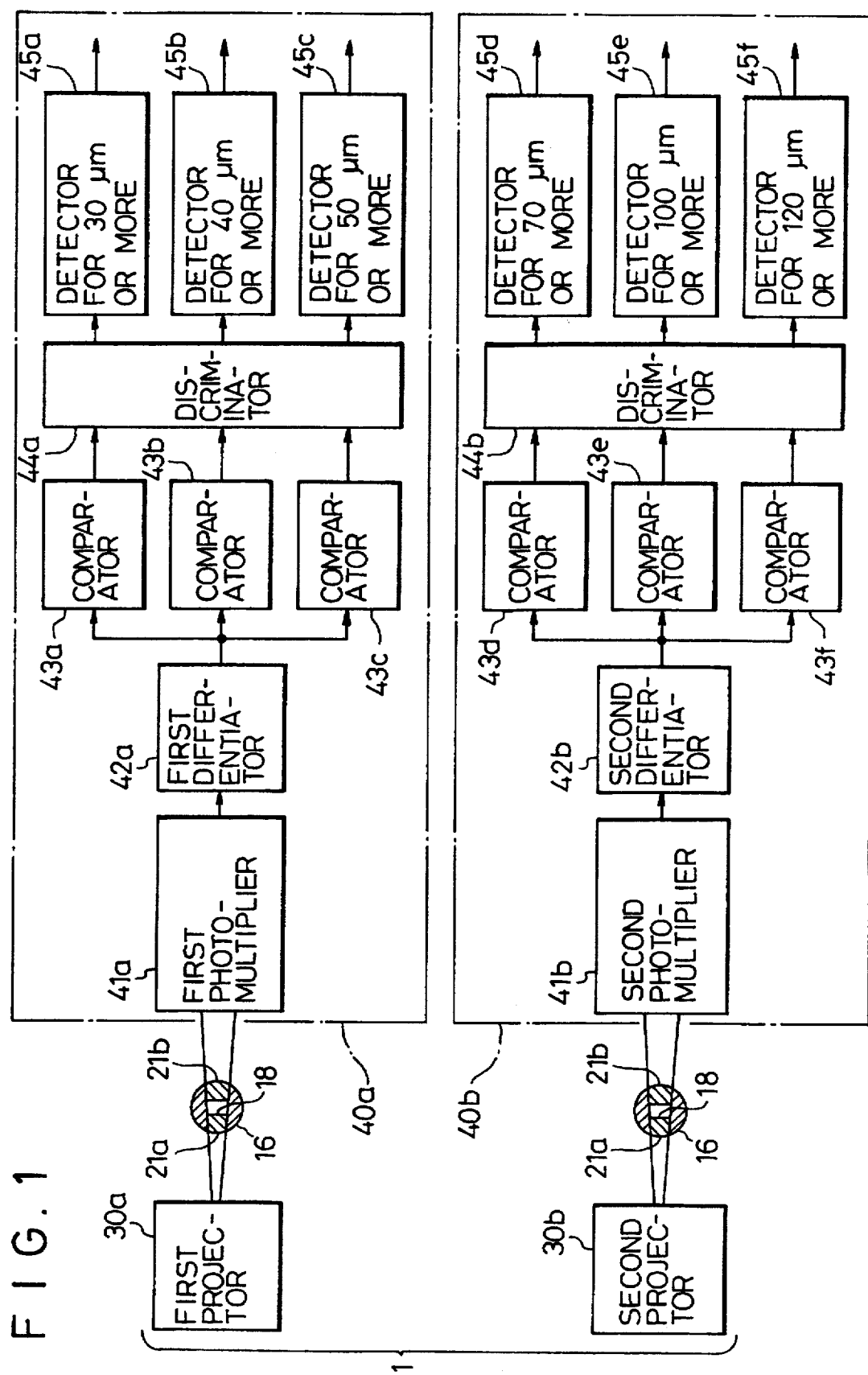
FIG. 1 is a block diagram showing an arrangement of a foreign matter detecting apparatus according to the first embodiment of the present invention.

FIG. 1 is a block diagram showing an arrangement of a foreign matter detecting apparatus according to the first embodiment of the present invention.

Referring to FIG. 1, the foreign matter detecting apparatus 1 according to the first embodiment is provided with two projectors and two light receivers. First and second projectors 30a and 30b are constructed in the same manner, comprising light sources 31a and 31b, optical scanning means 32a and 32b, and condensing lenses 33a and 33b, respectively (see FIGS. 2 and 3).

Each of the foreign matter detecting apparatuses according to the following embodiments is attached to, for example, a plastic extruder 11. The detecting apparatus is used to detect foreign matters in a molten resin, or plastic, which is formed by means of the plastic extruder 11 and is adapted to cover a high-voltage cable.

Figure 2:
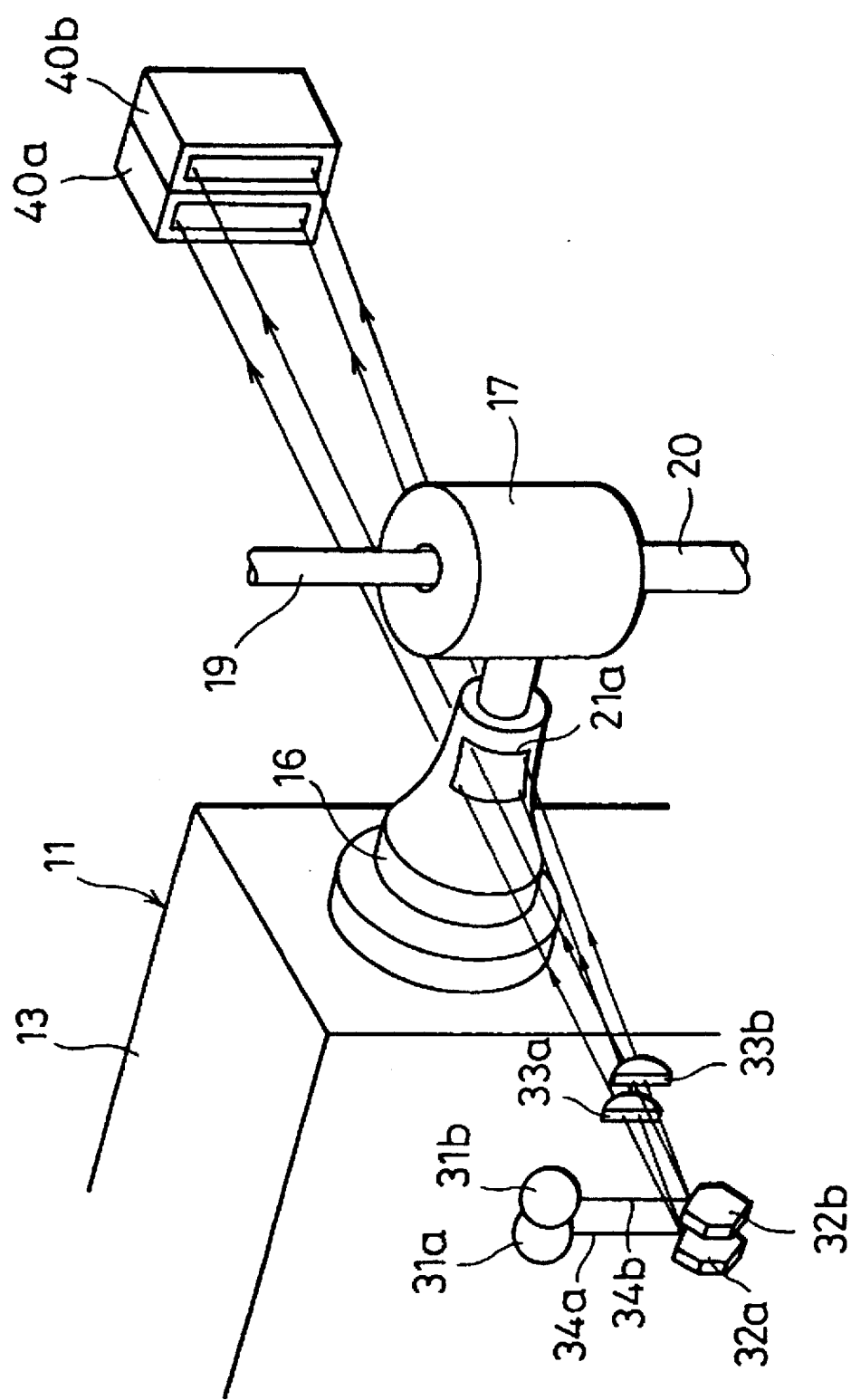
FIG. 2 is a perspective view showing an outline of the apparatus of FIG. 1.

In the plastic extruder 11, a screw (not shown) is housed in an extruder body 13 shown in FIG. 2. A crosshead 17 is connected to the front end of the extruder body 13 through an adapter 16. As the screw rotates, the plastic in the extruder body 13 is extruded therefrom and supplied to the crosshead 17 via a plastic passage 18 in the adapter 16. Then, the plastic is extruded onto the outer peripheral surface of a conductor 19 which vertically penetrates the crosshead 17, whereby a cable 20 is manufactured. In this plastic extruder 11, light transmitting portions 21a and 21b are formed in opposite positions with part of the plastic passage 18 with respect to the longitudinal direction thereof between them, substantially in the central portion of the adapter 16.

The light transmitting portions 21a and 21b are substantially as high as the plastic passage 18 (see FIG. 3). Also, the portions 21a and 21b are wide enough to allow two light beams emitted from the first and second projectors 30a and 30b to be transmitted without interfering with each other (see FIG. 2).

The light sources 31a and 31b of the first and second projectors 30a and 30b are made of, for example, laser diodes, such as gas or solid lasers, or light emitting diodes. The optical scanning means 32a and 32b are made of, for example, rotating or oscillating mirrors, such as polygon mirrors. In this embodiment, the first and second projectors 30a and 30b are synchronized with each other. Thus, according to this embodiment, the optical scanning means 32a and 32b successively synchronously scan their corresponding parts of the plastic passage 18 from top to bottom through the light transmitting portion 21a, with light beams 34a and 34b emitted from the light source 31a and 31b (see FIG. 3), and apply the beams 34a and 34b to the one light transmitting portion 21a of the adapter 16.

The foci of the condensing lenses 33a and 33b are set so that the incident light beams 34a and 34b converge into different convergence diameters substantially in the center of the plastic passage 18 with respect to the direction of light transmission. In this embodiment, for example, the foci of the lenses 33a and 33b are adjusted so that the light beams 34a and 34b are converged to diameters of 50 μm and 120 μm, respectively.

Thus, the light beams emitted from the first and second projectors 30a and 30b are transmitted through the one light transmitting portion 21a, cross parts of the plastic passage 18 so as to be transmitted through the plastic in the passage 18, and are delivered from the other light transmitting portion 21b to be received by external light receivers 40a and 40b, which will be mentioned later.

The first and second light receivers 40a and 40b are constructed in the same manner, comprising first and second photomultipliers 41a and 41b, first and second differentiators 42a and 42b, comparators 43a to 43c and 43d to 43f, discriminators 44a and 44b connected to the comparators 43a to 43c and 43d to 43f, and detectors 45a to 45c and 45d to 45f arranged corresponding to the comparators and connected to the discriminators 44a and 44b, respectively (see FIG. 1).

The first and second photomultipliers 41a and 41b receive the light beams transmitted through the plastic passage 18, and photoelectrically convert received light quantities which vary depending on the intensities of the light beams. Thus, if any foreign matter exists in the plastic flowing through the plastic passage 18, the intensities of the light beams passing through the passage 18 are subject to variation, so that the received light quantities vary depending on the light intensities. Accordingly, the photomultipliers 41a and 41b photoelectrically convert the received light quantities which vary depending on the intensities of the light beams. More specifically, the received light quantity in the first photomultiplier 41a varies considerably with a foreign matter having a diameter of 50 μm or less, while the received light quantity in the second photomultiplier 41b varies considerably with a foreign matter having a diameter of 70 to 120 μm.

The first and second differentiators 42a and 42b obtain differential waveforms of the changes of the received light quantities. If any foreign matter exists in the plastic, the levels of the peak values of the differential waveforms are obtained substantially in proportion to the size of the foreign matter.

Different threshold values corresponding to the size of the foreign matter to be detected are previously set in the comparators 43a to 43a and 43d to 43f. The comparators 43a to 43a and 43d to 43f compare the peak values of the inputted differential waveforms with the threshold values, and deliver the results of comparison to the discriminators 44a and 44b. More specifically, the comparators 43a, 43b and 43c check the foreign matter size to see if it is not smaller than peak values 30 μm, 40 μm, and 50 μm, respectively.

Further, the comparators 43d, 43e and 43f check the foreign matter size to see if it is not smaller than peak values 70 μm, 100 μm, and 120 μm, respectively. If the peak values of the differential waveforms are not smaller than the set threshold values, the comparators 43a to 43a and 43d to 43f deliver the results of comparison (e.g., high-level signals) to the discriminators 44a and 44b.

The discriminators 43a and 44b set the order of priority for the comparators 43a to 43a and 43d to 43f in advance. More specifically, the discriminator 44a gives the highest priority to the comparator 43c, second priority to the comparator 43d, and lowest priority to the comparator 43a. Likewise, the discriminator 44b gives the highest priority to the comparator 43f, second priority to the comparator 43e, and lowest priority to the comparator 43d. On receiving the results of comparison from the comparators, each discriminator discriminates the comparison result from the comparator of the highest priority based on the set order of priority, and delivers only the discriminated comparison result to the detector which corresponds to the comparator concerned.

Based on the results of comparison received from the discriminators 44a and 44b, the detectors 45a to 45c and 45d to 45f output detection signals, and give an alarm indicative of the foreign matter size concerned or display the foreign matter size, for example.

Figure 4A:
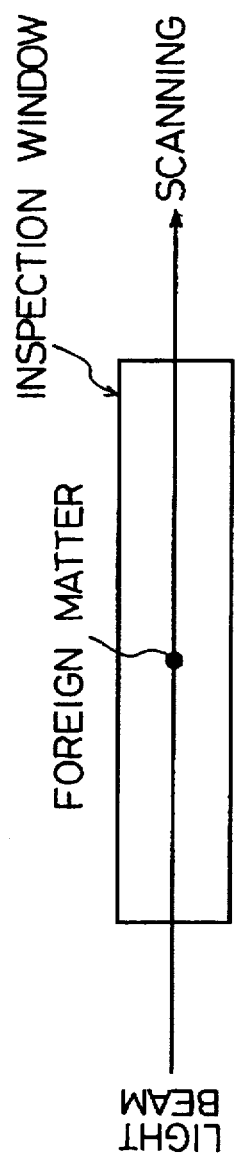
FIGS. 4A to 4C show principal waveforms produced by projectors and light receivers shown in FIG. 1.
Figure 4B:
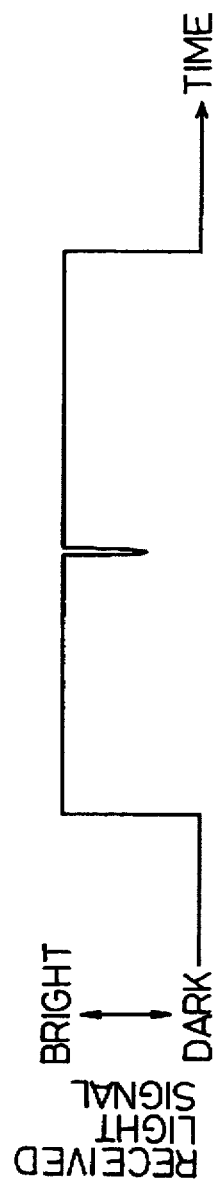
Figure 4C:
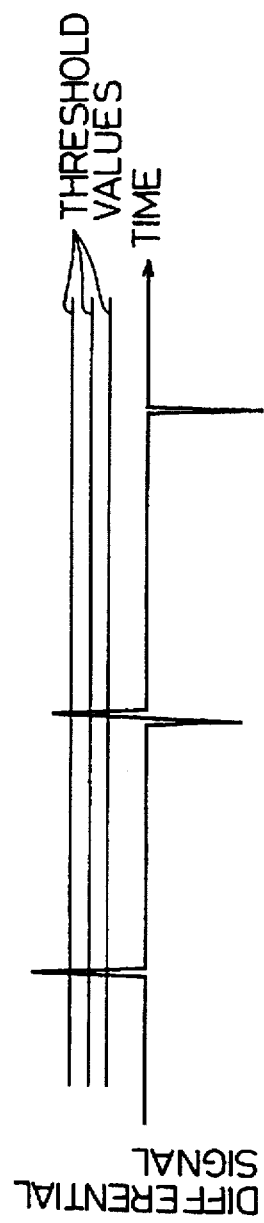

Referring now to the waveforms of FIGS. 4A to 4C, the operation of the foreign matter detecting apparatus shown in FIG. 1 is described. For ease of illustration, FIGS. 4A to 4C show waveforms based on one of the detectors and one of the light receivers.

In detecting a foreign matter, if any, the first and second projectors 30a and 30b synchronously apply the light beams 34a and 34b with convergence diameters of 50 μm and 120 μm, respectively, to the plastic in the plastic passage 18 through the light transmitting portions 21, as shown in FIG. 4A. An inspection window shown in FIG. 4A corresponds to a region of the plastic passage 18 to be scanned with a light beam, and the beam scanning direction is represented as a transverse direction compared with the scanning time.

Transmitted light beams are received individually by the first and second photomultipliers 41a and 41b of the light receivers 40a and 40b, and are photoelectrically converted into a voltage signals (received light signals) which correspond to the light intensities (see FIG. 4B). Then, the first and second differentiators 42a and 42b obtain differential waveforms of the changes of the received light quantities in accordance with the received light signals, and deliver differential signals composed of the differential waveforms to the comparators 43a to 43c and 43d to 43f. If a foreign matter involved in the plastic has a size not smaller than 30 μm and smaller than 70 μm, for example, a differential signal such as the one shown in FIG. 4C is obtained by the first differentiator 42a. If the foreign matter has a size not smaller than 70 μm, for example, a differential signal such as the one shown in FIG. 4C is obtained by the second differentiator 42b.

Then, the peak value of the differential signal is applied to the comparators 43a to 43c and 43d to 43f, whereupon it is compared with the three preset threshold values. In the light receiver 40a, the lowest of the three threshold values shown in FIG. 4C is set in the comparator 43a, a medium threshold value in the comparator 43b, and the highest in the comparator 43c. In the light receiver 40b, the lowest of the three threshold values shown in FIG. 4C is set in the comparator 43d, a medium threshold value in the comparator 43e, and the highest in the comparator 43f.

If the foreign matter has a size not smaller than 30 μm, the comparison result from the comparator 43a is delivered to the discriminator 43a. If the foreign matter has a size not smaller than 40 μm, moreover, the comparison results from the comparators 43a and 43d are delivered to the discriminator 44a. If the foreign matter has a size not smaller than 50 μm, furthermore, the comparison results from the comparators 43a to 43a are delivered to the discriminator 44a.

Likewise, if the foreign matter has a size not smaller than 70 μm, the comparison result from the comparator 43d is delivered to the discriminator 44b. If the foreign matter has a size not smaller than 100 μm, moreover, the comparison results from the comparators 43d and 43e are delivered to the discriminator 44b. If the foreign matter has a size not smaller than 120 μm, furthermore, the comparison results from the comparators 43d to 43f are delivered to the discriminator 44b.

On receiving the results of comparison from the comparators 43a to 43a and 43d to 43f, the discriminators 44a and 44b discriminate the comparison result from the comparator of the highest priority based on the set order of priority, and deliver only the discriminated comparison result to a detector which corresponds to the comparator concerned.

On receiving the comparison result, one of the detectors 45a to 45c and 45d to 45f outputs a detection signal, and gives an alarm indicative of the foreign matter size, or displays the foreign matter size concerned.

Thus, according to this embodiment, a foreign matter, if any, contained in a molten resin is detected by means of two light beams with different convergence diameters, so that the presence and size of the foreign matter can be detected accurately from the peak values of measured received light quantities.

Although two light beams with different convergence diameters are used according to this embodiment, the present invention is not limited to this arrangement, and the foreign matter detection may be also achieved by using three or more light beams with different convergence diameters.

The following is a description of the second embodiment in which the length of a foreign matter is detected. In this embodiment, as shown in FIG. 5, an inspection window of a plastic passage 18 is segmented in the light beam scanning direction, thereby providing a plurality of light beam scanning areas (five areas 46a to 46e in this case).

Figure 6:
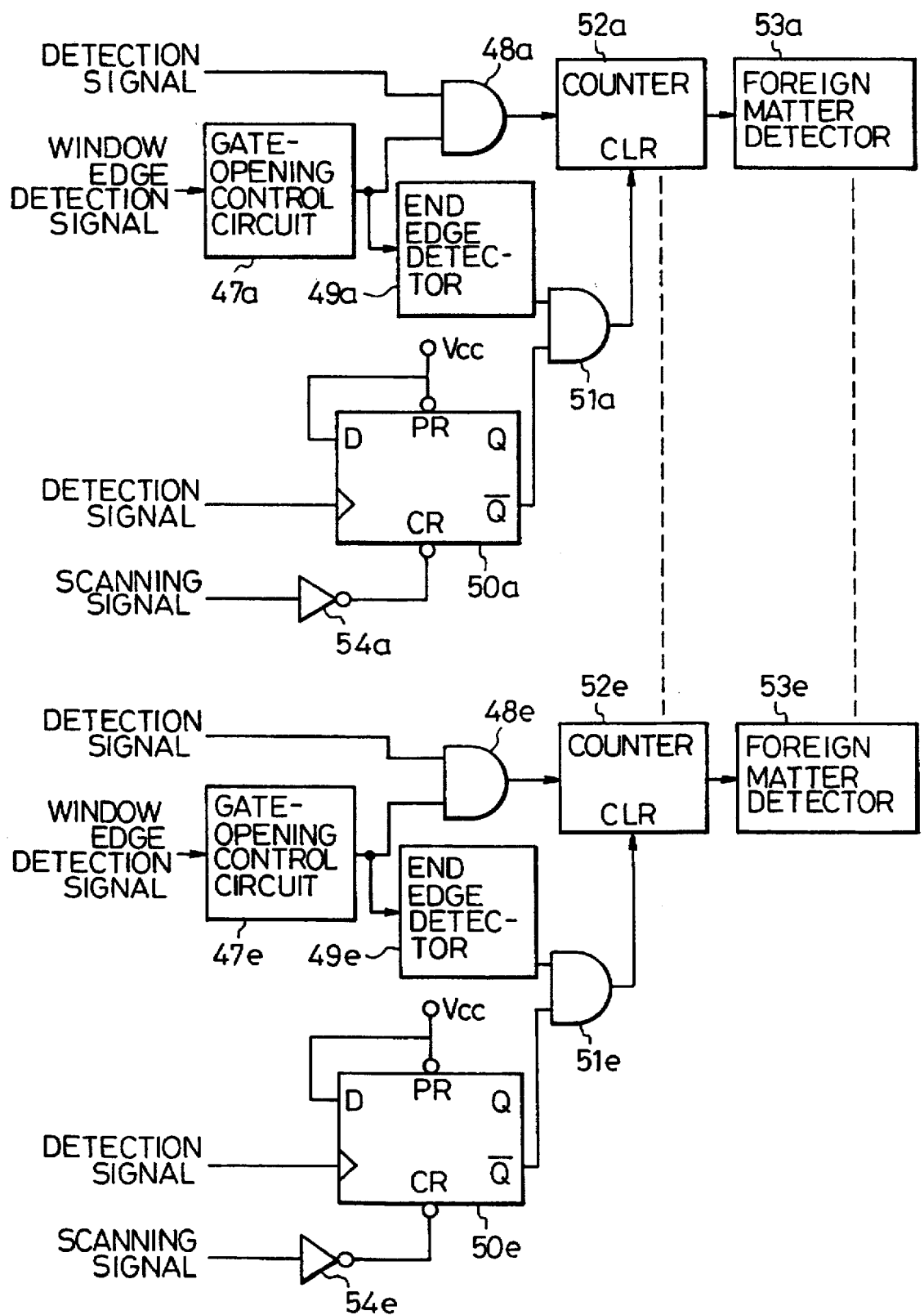
FIG. 6 is a block diagram showing an arrangement of principal parts of a foreign matter detecting apparatus according to the second embodiment of the invention.

FIG. 6 is a block diagram showing an arrangement of principal parts of a foreign matter detecting apparatus according to the second embodiment. For other parts, this apparatus is constructed in the manner shown in FIG. 1. Although actual principal parts for detecting the foreign matter length are arranged corresponding to the scanning areas 46a to 46e shown in FIG. 5, FIG. 6 shows only those principal parts which correspond to the scanning areas 46a and 46e, for simplicity of illustration. Principal parts which correspond to the scanning areas 46b, 46c and 46d are constructed in the same manner as the ones which correspond to the areas 46a and 46e.

More specifically, the principal parts include gate-opening control circuits 47a to 47e, AND gates 48a to 48e connected to the circuits 47a to 47e, respectively, end edge detectors 49a to 49e connected to the circuits 47a to 47e, respectively, and flip-flops 50a to 50e. The principal parts further include AND gates 51a to 51e connected to the detectors 49a to 49e and the flip-flops 50a to 50e, respectively, counters 52a to 52e connected to the AND gates 48a to 48e and 51a to 51e, respectively, foreign matter detectors 53a to 53e connected to the counters 52a to 52e, respectively, and inverters 54a to 54e connected to the flip-flops 50a to 50e, respectively.

The gate-opening control circuits 47a to 47e are connected to one (e.g., differentiator 42a) of the differentiators 42a and 42b shown in FIG. 1. The control circuits 47a to 47e are supplied with a window edge detection signal (first leading-edge pulse shown in FIG. 4C) from the differentiator 42a. The control circuits 47a to 47e, which are provided corresponding to the scanning areas 46a to 46e, respectively, are used to set the times when scanned light beams pass through the scanning areas 46a to 46e. Thus, when supplied with the window edge detection signal, the control circuits 47a to 47e deliver gate-opening signals individually to the AND gates 48a to 48e and the end edge detectors 49a to 49e for lengths corresponding to the respective widths of the scanning areas 46a to 46e in the scanning direction. In this manner, the AND gates 48a to 48e are opened in succession.

The AND gates 48a to 48e are supplied with the gate-opening signals and the detection signals from the detectors 45a to 45f shown in FIG. 1. If the AND gates 48a to 48e are supplied with the detection signals when they are open, therefore, they deliver detection signal to the counters 52a to 52e, respectively.

The end edge detectors 49a to 49e detect the end edges of the gate-opening signals being inputted. When the end edges are detected, the circuits 49a to 49e deliver detection signals, such as the one shown in FIG. 7A, to the AND gates 51a to 51e, respectively.

The inverters 54a to 54e convert scanning signals, such as the one shown in FIG. 7B, into inverted signals, such as the one shown in FIG. 7C, and output the inverted signals.

The inverted signals are applied individually to the respective clear terminals CR of the flip-flops 50a to 50e, and detection signals, such as the one shown in FIG. 7D, to their clock terminals. These detection signals are signals delivered from the detectors 45a to 45f shown in FIG. 1 (identical with the detection signals applied to the AND gates 48a to 48e). When supplied with the inverted signals, therefore, the flip-flops 50a to 50e clear the outputs to the AND gates 51a to 51e. When supplied with the detection signals, on the other hand, the flip-flops 50a to 50e deliver low-level signals to the AND gates 51a to 51e, respectively (see FIG. 7E).

If the end edge detection signals are delivered from the end edge detectors 49a to 49e when the outputs from the flip-flops 50a to 50e are on the high level, the AND gates 51a to 51e deliver gate outputs, such as the one shown in FIG. 7F, thereby clearing count values in the counters 52a to 52e.

When the counters 52a to 52e are supplied with the detection signals from the AND gates 48a to 48e, they start counting, and deliver their count values to the foreign matter detectors 53a to 53e, respectively. Thus, the counters 52a to 52e perform counting when the detection signals are outputted while the light beams are moving in their corresponding scanning areas. If the detection signals are not outputted while the light beams are moving in the corresponding scanning areas, on the other hand, the counters 52a to 52e clear the count values.

The foreign matter detectors 53a to 53e detect the length of a foreign matter in accordance with the input count values delivered thereto.

In order to determine the length of the foreign matter, it is necessary to measure the flow rate of the foreign matter. It is difficult, however, to measure the flow rate of a minute foreign matter. In the case where the flow rate of the plastic is known, therefore, the flow rate of the foreign matter moving in the plastic passage 18 is regarded as substantially equal to that of the plastic. The flow rate of the plastic can be measured by means of, for example, a flowmeter which can be mounted in the extruder.

If the plastic flow rate, the light scanning frequency of the projectors, the light beam convergence diameter, and the length of the foreign matter in the longitudinal direction of the passage are 10 mm/sec, 4,000 cycles/sec, 50 μm, and 200 μm, respectively, for example, then the foreign matter moves for a distance given by 10 mm/4,000=2.5 μm with every scanning cycle. Accordingly, the length of that portion of the foreign matter which is entirely covered by the light beam spot of 50-μm diameter is a length obtained by subtracting 25 μm twice (for the opposite ends) from the length of the foreign matter, that is, 200−50=150 (μm). Since the scanning frequency is given by 150/2.5=60, the foreign matter can be securely caught 60 times. Even in case detection levels for the foreign matter cannot be distinguished from noises, therefore, any substance which is continuously detected a plurality of times can be identified as a minute elongate foreign matter.

If the distance of movement covered for each scanning cycle is $v$, there is a relation $$v = V/S,$$

where V and S are the flow rate (mm/sec) and the scanning frequency (cycles/sac), respectively. A detection frequency N is given by $$N = (L-D)/v,$$

where L and D are the length of a foreign matter in the longitudinal direction and the convergence diameter (μm) of the light beam spot, respectively. Based on this equation and the input count values, the foreign matter detectors 53a to 53e can obtain the length of the foreign matter moving in the plastic passage 18.

Thus, according to the second embodiment, when the window edge detection signal is inputted after the start-side end of the window is detected by the window edge detection signal, the gate-opening control circuits 47a to 47e output gate-opening signals after the passage of a predetermined time, and keep the AND gates 48a to 48e open for the times corresponding to the corresponding scanning area widths.

When the detection signals are delivered from the detectors 45a to 45f with the aforesaid gates open, the counters 52a to 52e start counting. The counters continue the counting while the detection signals are being inputted in succession. When the detection signals are interrupted, as shown in FIG. 7D, high-level outputs are produced in the AND gates 51a to 51e (see FIG. 7) in response to the outputs of the end edge detectors 49a to 49e and the flip-flops 50a to 50e (see FIGS. 7A and 7E). Thereupon, the counters 52a to 52e are reset, so that the count values are cleared.

Thus, in this embodiment, the counters count the detection signals which are generated in succession, and the foreign matter detectors detect the length of foreign matters. Accordingly, even minute elongate foreign matters, such as fibers, which cannot be easily distinguished from the noises, can be discriminated, and their lengths can be also detected.

In the second embodiment, the projectors and the light receivers are provided in two sets. Alternatively, however, they may be arranged in one or three sets or more according to the present invention. In any of these cases, the length of a foreign matter can be detected with ease.

According to the second embodiment, moreover, the inspection window of the plastic passage is segmented into five scanning areas. Alternatively, however, the number of these segments may be increased to improve the accuracy of detection of the foreign matter length.

There is a possibility of a foreign matter bestriding the boundary between two scanning areas. If detection signals are produced in two proximate scanning areas, therefore, it is advisable to count the signals by means of the counters to detect the foreign matter length, assuming the signals to have been detected in one area.

Ideally, the detection signals should, without fail, be outputted by continuous scanning. However, a foreign matter does not always have a uniform width in the longitudinal direction. In actual detection, therefore, a foreign matter may possibly be missed several times. Accordingly, detection of an elongate foreign matter need not always be continuous, and discontinuous detection may be effected at some frequency so that the elongate foreign matter can be securely discriminated in comparison with an actually existing foreign matter.

Although a plurality of projectors and light receivers are used according to the embodiments described above, the present invention is not limited to this arrangement, and the accuracy of foreign matter detection can be improved by using a foreign matter detecting apparatus which is provided with a combination of one projector 60 and one light receiver 70, as shown in FIGS. 8 to 11. For simplicity of illustration, like reference numerals are used to designate like portions throughout the drawings.

Figure 8:
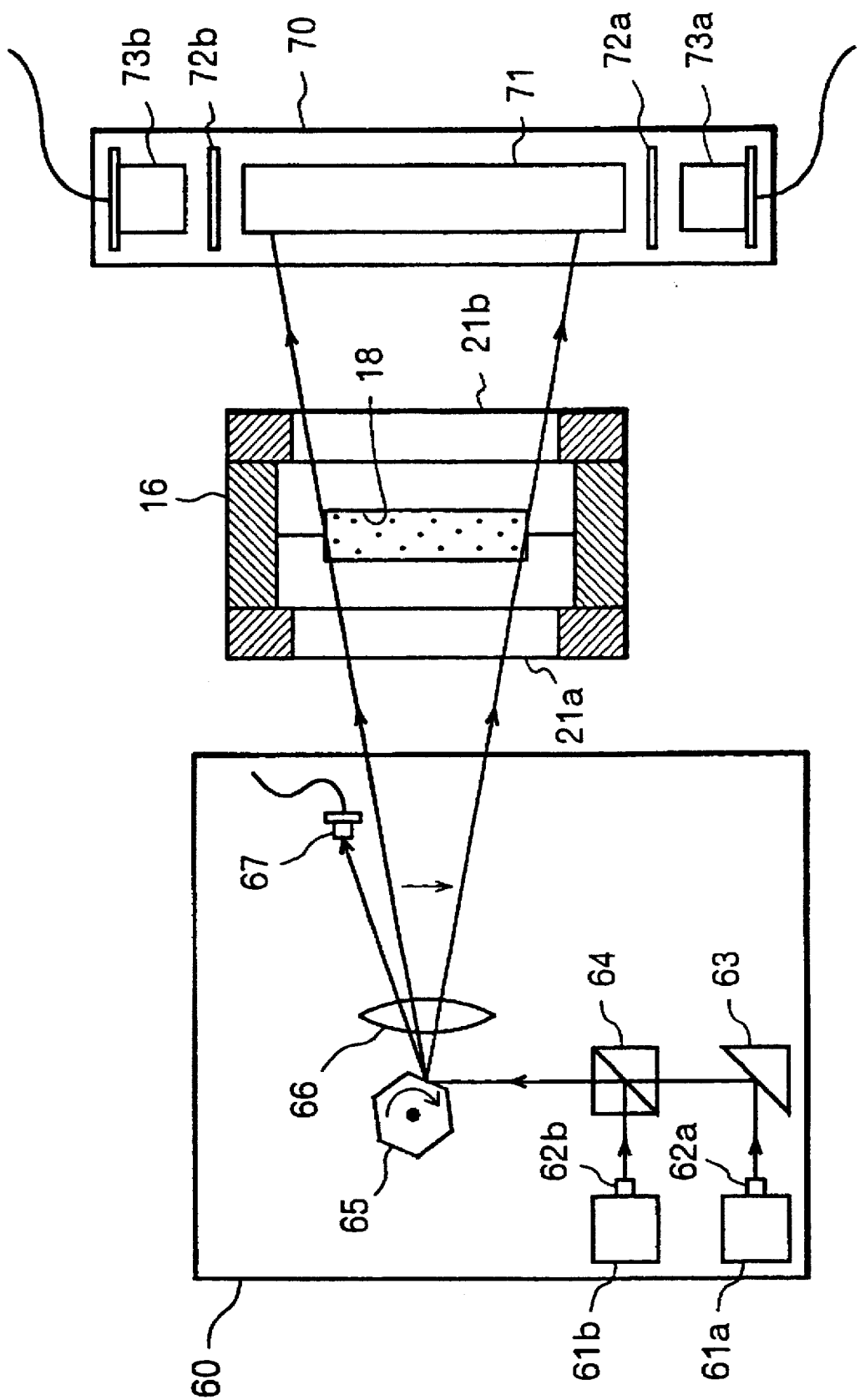
FIG. 8 is a diagram showing an arrangement of principal parts of a foreign matter detecting apparatus according to the third embodiment of the invention.

Referring to FIG. 8, the projector 60 according to this third embodiment comprises two light sources 61a and 61b of different types, beam expanders 62a and 62b attached to the light sources 61a and 61b, respectively, a mirror 63 for reflecting a light beam from the light source 61a, and a beam splitter 64 for coupling light beams emitted from the light sources 61a and 61b. The projector 60 further comprises a polygon scanner 65 formed of a polygon mirror for scanning the composite light beam, a condensing lens 66 for converging the light beam, and a light receiving element 67 for outputting a trigger signal indicative of the start of inspection.

The light sources 61a and 61b are made of, for example, an He-Ne laser with a wavelength of 632.8 nm and an Ar laser with a wavelength of 488 nm, respectively, and output light beams with these different wavelengths. The diameters of the light beams from the light sources 61a and 61b are enlarged by means of the beam expanders 62a and 62b, respectively. The expanded light beams are coupled into a composite light beam by the mirror 63 and the beam splitter 64, and the composite light beam is scanned by the polygon scanner 65 and applied to an adapter 16 through the condensing lens 66. The minimum convergence radius of a light beam tends to vary in inverse proportion to the radius of incidence on the condensing lens. According to this embodiment, therefore, the light beams from the light sources 61a and 61b are previously adjusted to predetermined convergence diameters in a plastic passage 18 by means of their corresponding beam expanders 62a and 62b.

Thus, the light beam emitted from the projector 60 is projected into the adapter 16 through one light transmitting portion 21a thereof, and crosses part of the plastic passage 18 so as to be transmitted through the plastic in the passage 18. The light beam delivered from the other light transmitting portion 21b of the adapter 16 is received as a transmitted light by an external light receiver 70.

The light receiver 70 comprises a light guide rod 71 for detecting the light transmitted through the plastic in the plastic passage 18 of the adapter 16 with every scanning cycle, band pass filters 72a and 72b for transmitting only those light beams from the light sources 61a and 61b which have specific wavelengths, and light receiving elements 73a and 73b formed of photomultipliers for photoelectrically converting the transmitted light beams. Further, the receiver 70, like the ones shown in FIG. 1, for example, comprises first and second differentiators 42a and 42b, comparators 43a to 43f, discriminators 44a and 44b, and detectors 45a to 45f. The discriminators 44a and 44b, which are supplied with the trigger signal from the light receiving element 67, can set a predetermined inspection range in response to the trigger signal, and discriminates a foreign matter within the set range.

For example, the band pass filter 72a transmits only those light beams with specific wavelengths which are emitted from the light source 61a, among the transmitted light beams (coupled light beams) detected by means of the light guide rod 71. On the other hand, the band pass filter 72b transmits only those light beams with specific wavelengths which are emitted from the light source 61b, out of the detected transmitted light beams. The light receiving element 73a photoelectrically converts the received light quantity which varies depending on the intensities of the light beams transmitted through the band pass filter 72a. Likewise, the light receiving element 73b photoelectrically converts the received light quantity which varies depending on the intensities of the light beams transmitted through the band pass filter 72b.

The first and second differentiators 42a and 42b obtain differential waveforms of the changes of the received light quantities, and deliver them to their corresponding comparators 43a to 43c and 43d to 43f. The comparators 43a to 43c and 43d to 43f compare the peak values of the inputted differential waveforms with threshold values therein, and deliver the results of comparison to the discriminators 44a and 44b.

Based on a previously set order of priority, the discriminators 44a and 44b deliver the results of comparison from the comparators to the detectors which correspond to the comparators. The detectors 45a to 45c and 45d to 45f output detection signals on the basis of the results of comparison received from the discriminators 44a and 44b.

Thus, in the third embodiment, light beams with different convergence diameters and wavelengths are coupled into a composite light beam by means of the projector, the composite light beam is applied to the plastic in the plastic passage, and the transmitted light beam is received and branched into light beams with wavelengths for the individual light sources by the light receiver. In consequence, according to this embodiment, light beams with different convergence diameters can be simultaneously applied to one and the same position.

Since the composite light beam is projected and received according to this embodiment, moreover, only one projector and one light receiver are enough for the purpose, so that the apparatus can be reduced in size and weight.

In this embodiment, moreover, a foreign matter contained in a molten resin is detected by properly branching coupled light beams with different convergence diameters by means of the filters for wavelength selection in the light receiver, so that the accuracy of foreign matter detection can be improved.

In this third embodiment, furthermore, the scanning system such as the polygon scanner is used singly, so that received light signals corresponding to the light beams are synchronized, so that signal processing for foreign matter detection is easy.

According to this embodiment, moreover, the transmitted light is branched into light beams with specific wavelengths by means of the band pass filters. Alternatively, however, the same effected can be obtained by using high and low pass filters, for example. According to the present invention, furthermore, a half mirror may be used in place of the beam splitter.

In cases where foreign matter to be detected includes semitransparent matter, the transmittance of light is affected by the color of such foreign matter, that is, the light transmittance depends on the light wavelength. Foreign matter to be detected may be black marks or red burn marks (hereinafter referred to as "resin burn marks") formed in a molten resin by heat, for example. Black marks scarcely transmit light therethrough and absorb light of nearly the entire wavelength range; therefore, such marks can be detected by using any desired light source because there is no particular restriction on the wavelength of the light beam from the light source. In the case of resin burn marks, however, if the He-Ne laser is used for the detection, the transmitted light beams are not liable to change in appearance due to their resemblance to the resin burn marks in color.

Preferably, in this case, light sources to be used are selected taking account of the transmittance of light with respect to different kinds of foreign matter (for example, light sources capable of emitting green or blue light beams with a wavelength of 550 nm or less are used for detecting resin burn marks). Thus, in this embodiment, even in the case where semitransparent foreign matters of different colors exist in the fluid to be detected, suitable light sources may be used to emit light with a wavelength such that the transmitted light beams show noticeable changes. By doing this, a light beam transmitted through a resin burn mark or a foreign matter of other kind can be easily changed, facilitating the detection of foreign matters of different kinds and improving the detection accuracy.

Figure 9:
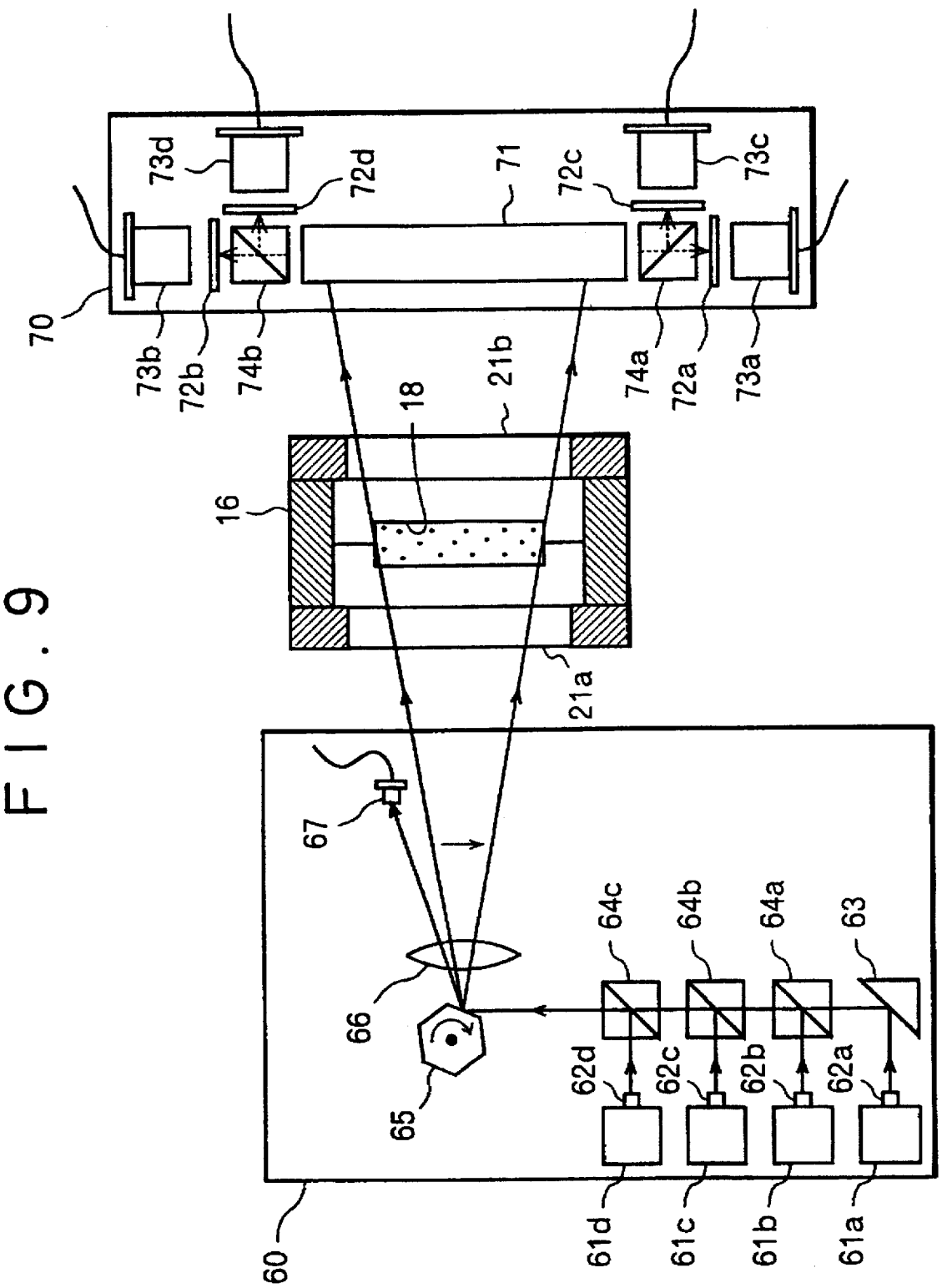
FIG. 9 is a diagram showing an arrangement of principal parts according to the fourth embodiment of the invention.

FIG. 9 is a diagram showing an arrangement of principal parts of a foreign matter detecting apparatus according to the fourth embodiment of the present invention. For simplicity of illustration, like reference numerals are used to designate like portions throughout the drawings.

The arrangement shown in FIG. 9 differs from the arrangement shown in FIG. 8 in that a projector 60 includes four light sources 61a to 61d which emit light beams of different frequencies, the diameters of the light beams are enlarged by means of their corresponding beam expanders 62a to 62d, and a composite light beam is coupled from the light beams with different frequencies and convergence diameters by means of beam splitters 64a to 64c. According to the fourth embodiment, moreover, a light receiver 70 has beam splitters 74a and 74b arranged individually at the opposite ends of a light guide rod 71, whereby a transmitted light beam (composite light beam) from a plastic passage 18 is diverged in four directions. Arranged in front of light receiving elements 73a to 73d are band pass filters 72a to 72d which correspond to the wavelengths of the light beams from the light sources 61a to 61d, respectively, whereby the detected transmitted light beam is branched into light beams with various wavelengths.

Thus, in the fourth embodiment, the four light beams of the different types are properly coupled, applied, and branched, and a foreign matter, if any, in a molten resin is detected in accordance with the varying quantities of the received branched light beams. In consequence, according to this embodiment, foreign matters can be detected more finely, so that the accuracy of foreign matter detection can be improved.

Although the number of types of the light sources used is two or four according the foregoing embodiments, the present invention is not limited to those embodiments, and light beams with different convergence diameters may be coupled by using three or five or more light sources and beam splitters which emit light beams with different frequencies.

Figure 10:
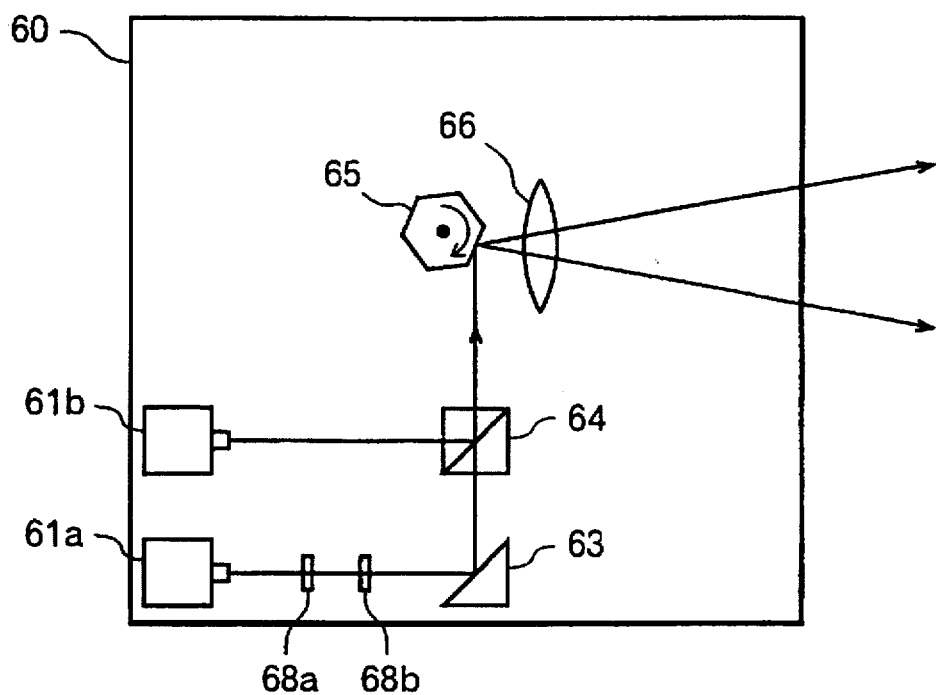
FIG. 10 is a diagram showing an arrangement of principal parts of a projector according to another embodiment of the invention.

FIG. 10 is a diagram showing an arrangement of principal parts of a projector according to another embodiment of the present invention.

In the projector 60 of this embodiment, as shown in FIG. 10, cylindrical lenses 68a and 68b are located in front of an optical scanning system (mirror 63) so that the convergence diameters of light beams in a molten resin can be varied. According to this embodiment, therefore, the convergence diameters of the light beams can be changed for each light source used.

Figure 11:
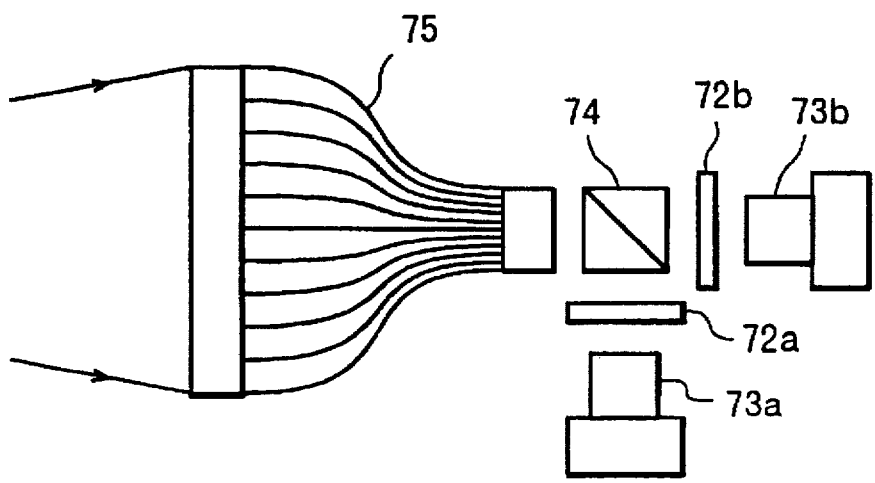
FIG. 11 is a diagram showing an arrangement of principal parts of a light receiver according to still another embodiment of the invention.

FIG. 11 is a diagram showing an arrangement of principal parts a light receiver according to another embodiment of the present invention.

In the light receiver of this embodiment, as shown in FIG. 11, a fiber bundle 75, which is composed of optical fibers arranged in the light beam scanning direction, is used in place of the light guide rod according to the foregoing embodiments. A transmitted light beam from a plastic passage is fetched by means of the fiber bundle 75, and is guided to light receiving elements 73a and 73b through a beam splitter 74 and band bass filters 72a and 72b. Thus, according to this embodiment, the transmitted light beam can be fetched by means of the fiber bundle used in place of the light guide rod, and the light receiver can be manufactured at lower cost than in the case where the light guide rod is used.

Referring now to FIGS. 12 to 16, a fifth embodiment of the present invention will be described in which the kinds of foreign matters are detected. In the description to follow, like reference numerals are used to designate like portions throughout the drawings for simplicity of illustration. The following is a description of a case in which a foreign matter detecting apparatus according to this embodiment is used to detect metallic foreign matters, such as aluminum, copper, iron etc., and fibrous foreign matters.

Figure 12:
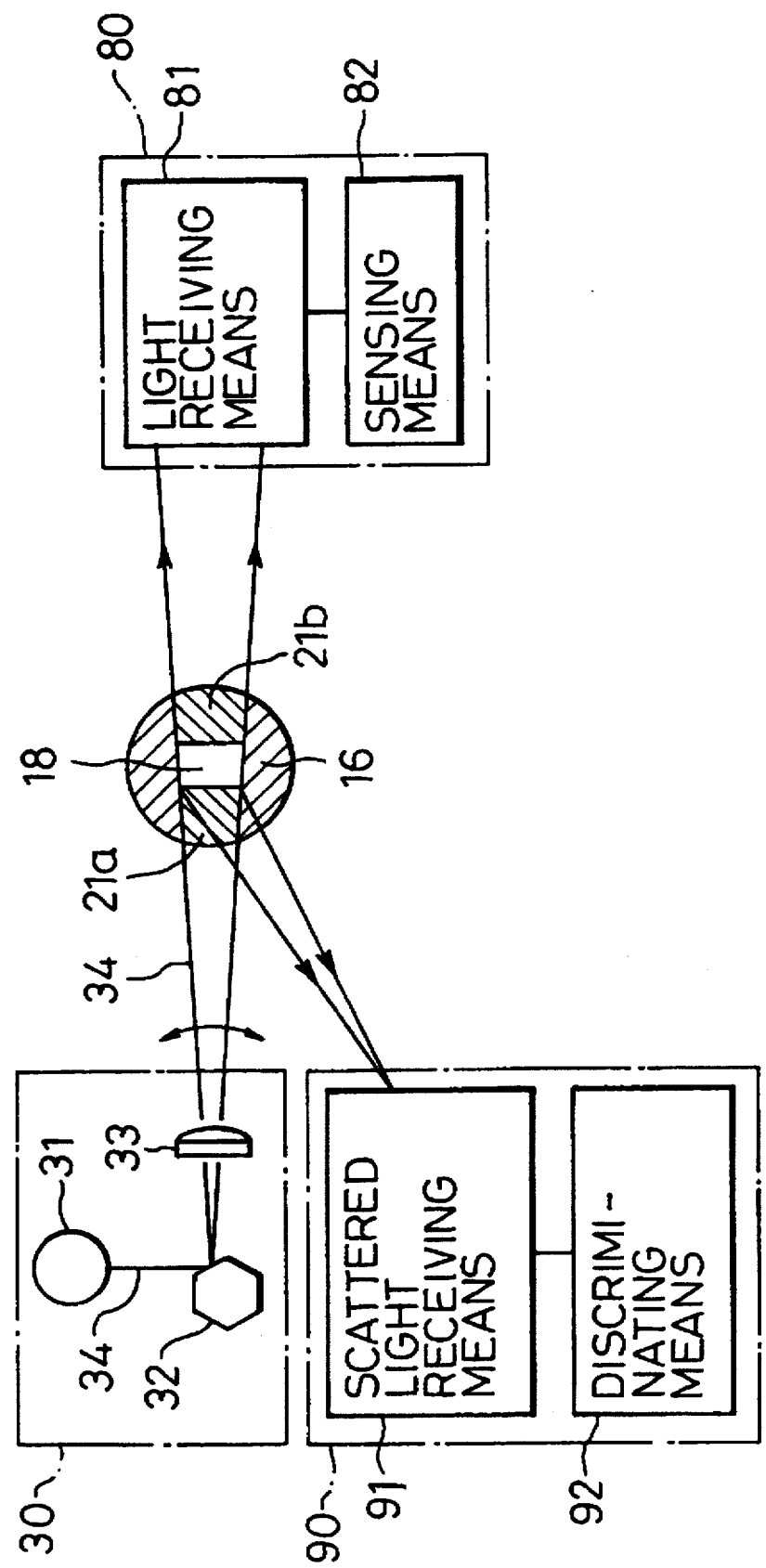
FIG. 12 is a block diagram showing an arrangement of a foreign matter detecting apparatus according to a fifth embodiment of the invention.
Figure 13:
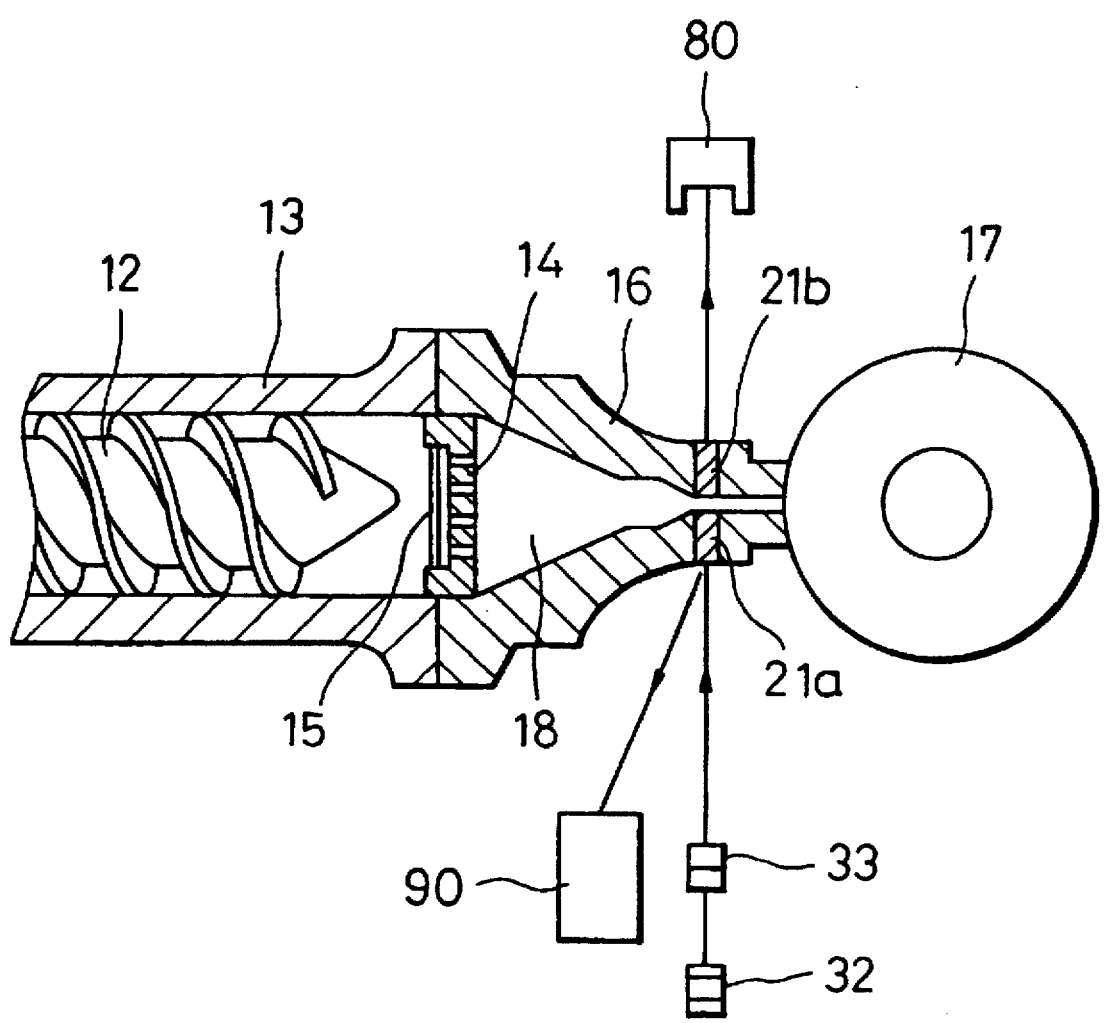
FIG. 13 is a sectional view showing an arrangement of principal parts shown in FIG. 12.

FIG. 12 is a block diagram showing an arrangement according to the fifth embodiment of the present invention. FIG. 13 is a sectional view showing an arrangement of principal parts shown in FIG. 12.

Referring to FIG. 12, there are shown a projector 30, a light receiver 80, and a scattered light receiver 90. Referring then to FIG. 13, a screw 12 is contained in a body 13 of a plastic extruder 11. As the screw 12 rotates, a plastic in the extruder body 13 is extruded therefrom through a mesh screen 14 for seizing foreign matters and a breaker plate 15. Then, the plastic is supplied to a crosshead 17 through a plastic passage 18 which is formed in an adapter 16.

The projector 30 comprises a light source 31, optical scanning means 32, and a condensing lens 33 (see FIGS. 12 and 13). In the projector 30, the scanning means 32 scans part of the plastic passage 18 from top to bottom with a light beam 34 emitted from the light source 31 which is formed of a laser, and applies the light beam 34 to one light transmitting portion 21a of the adapter 16. The focus of the condensing lens 33 is adjusted so that the incident light beam 34 is converged to a predetermined convergence diameter substantially in the center of the plastic passage 18 with respect to the direction of light transmission. In this fifth embodiment, the focus of the lens 33 is adjusted so that the light beam is converged to a diameter of 100 μm, for example. The light transmitting portions 21a and 21b are wide enough to allow the passage of the light beam.

The light receiver 80 comprises light receiving means 81 for photoelectrically converting the incident light beam, and sensing means 82 for detecting the presence and size of a foreign matter, if any, in the plastic in accordance with the change of the level of the converted received light signal.

Figure 14:
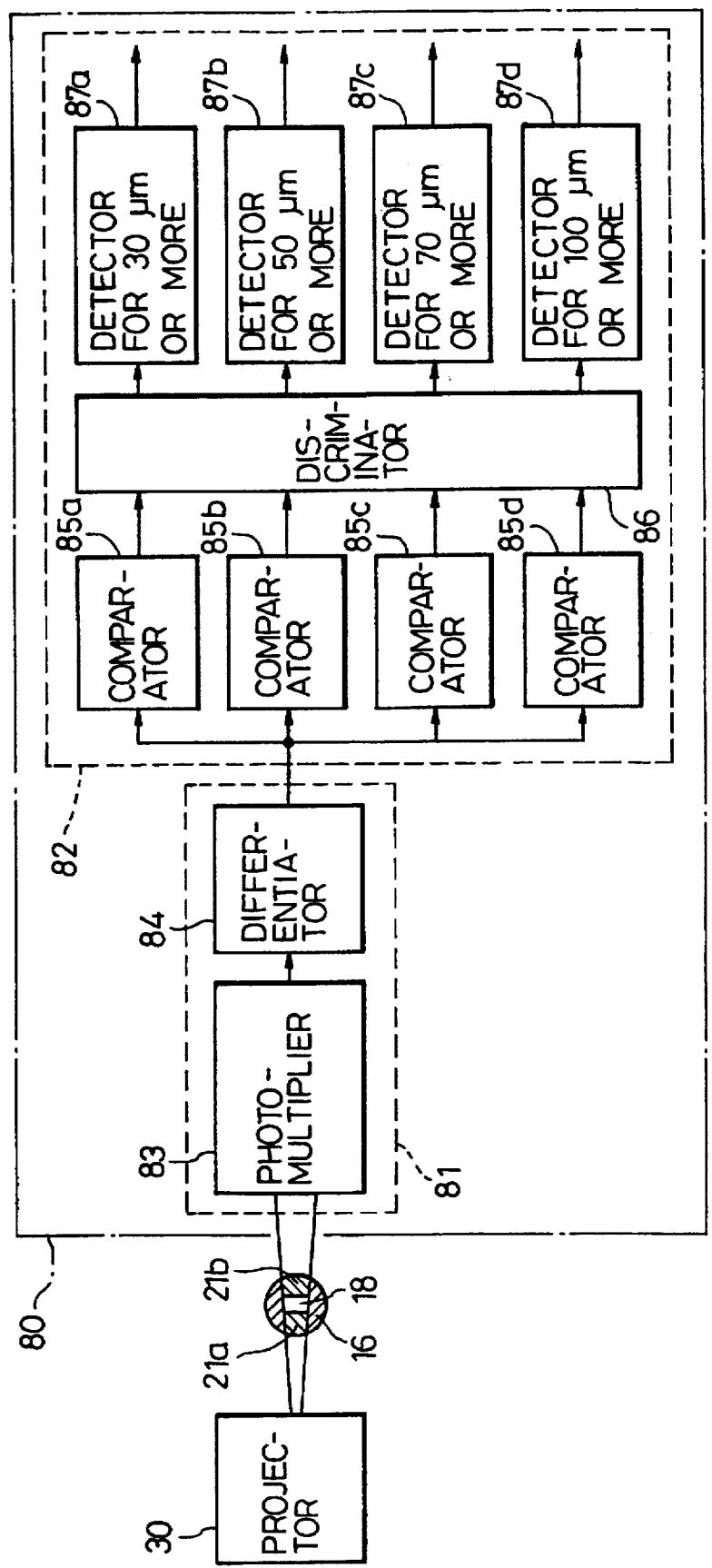
FIG. 14 is a block diagram showing an arrangement of light receiving means and detecting means shown in FIG. 12.

As shown in the block diagram of FIG. 14, the light receiving means 81 includes a photomultiplier 83 and a differentiator 84. The sensing means 82 includes four comparators 85a to 85d connected to the differentiator 84, a discriminator 86 connected to the comparators 85a to 85d, and detectors 87a to 87d arranged corresponding to the comparators 85a to 85d, respectively, and connected to the discriminator 86. If there is any foreign matter in the plastic, such foreign matter affects the light beam transmitting therethrough, and thus the level of the received light signal obtained by the light receiving means 81 is lowered at a point corresponding to the foreign matter when the plastic is scanned by means of the laser.

The photomultiplier 83 receives the light beam transmitted through the plastic passage 18, and photoelectrically converts the received light quantity which varies depending on the intensity of the light beam if any foreign matter exists in the plastic flowing through the plastic passage 18.

The differentiator 84 obtains a differential waveform of the change of the received light quantity. If there is any foreign matter in the plastic, in this case, the peak value of the differential waveform is substantially proportional to the size of the foreign matter, so that the presence and size of the foreign matter can be detected.

Different threshold values corresponding to the size of the foreign matter to be detected are previously set in the comparators 85a to 85d. The comparators 85a to 85d compare the peak value of the inputted differential waveform with the threshold values, and deliver the results of comparison to the discriminator 86. More specifically, the comparators 85a, 85b, 85c and 85d check the foreign matter size to see if it is not smaller than 30 μm, 50 μm, 70 μm, and 100 μm, respectively. If the peak value of the differential waveform is not smaller than the set threshold values, the comparators 85a to 85d deliver a result of the comparison (e.g., high-level signals) to the discriminator 86.

The discriminator 86 sets the order of priority for the four comparators 85a to 85d in advance. More specifically, the discriminator 86 gives the highest priority to the comparator 85d, and second, third, and lowest to the comparators 85c, 85b and 85a, respectively. On receiving the results of comparison from the comparators, the discriminator 86 discriminates the comparison result from the comparator of the highest priority based on the set order of priority, and delivers only the discriminated comparison result to the detector which corresponds to the comparator concerned.

Based on the results of comparison received from the discriminator 86, the detectors 87a to 87d output detection signals, and can give an alarm indicative of the foreign matter size concerned, for example, or display the foreign matter size. Also, these detection signals are delivered to discriminating means 92 of the scattered light receiver 90.

The scattered light receiver 90 comprises scattered light receiving means 91 for photoelectrically converting reflected scattered light beams, and the discriminating means 92 for detecting the presence and size of a foreign matter, if any, in the plastic in accordance with the change of the level of the converted received light signal (see FIG. 12). The scattered light receiver 90 may be attached to the projector 30 or located in any position where the scattered light beams can be received in accordance with the shape of the plastic passage.

Figure 15:
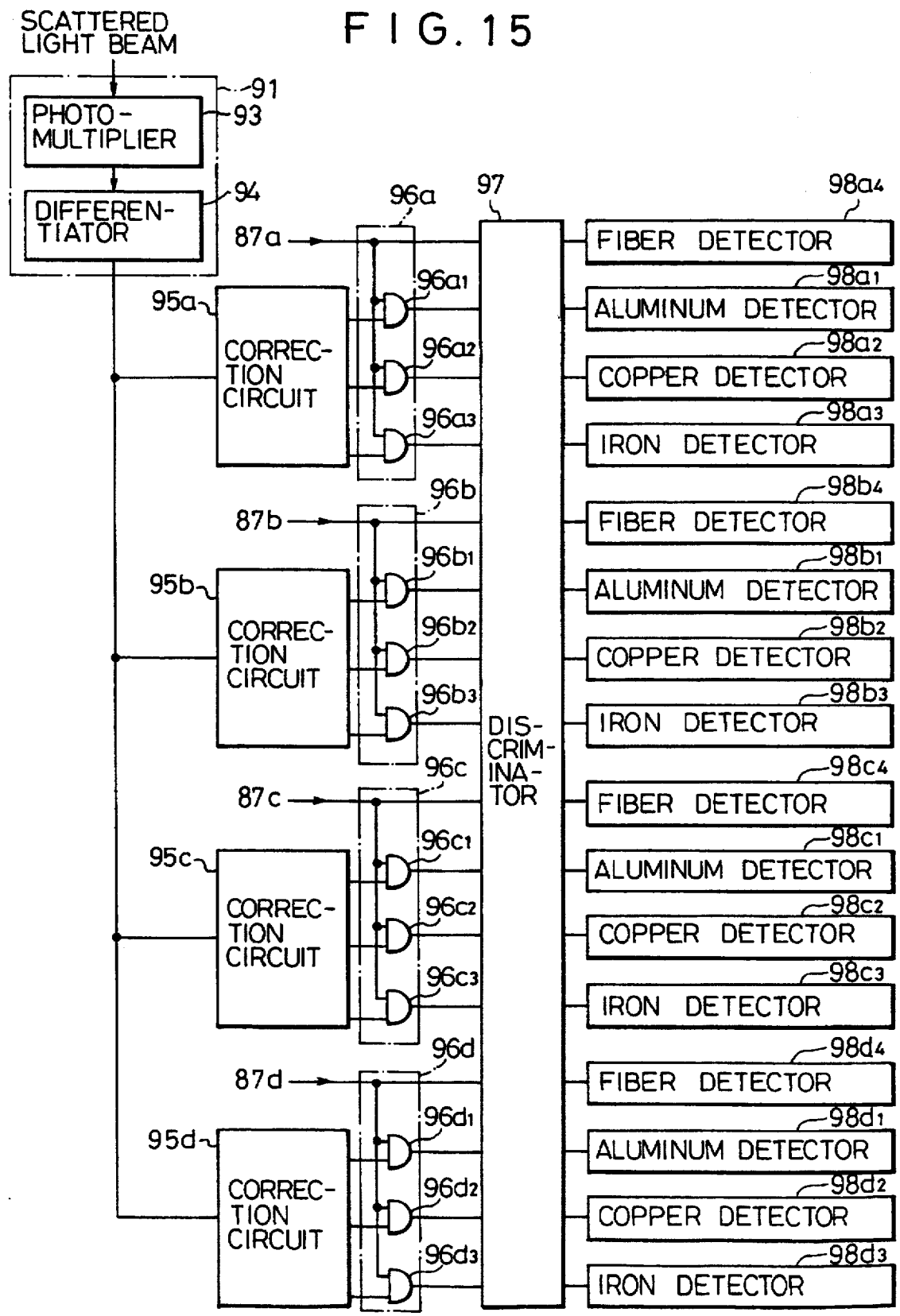
FIG. 15 is a block diagram showing an arrangement of scattered light receiving means and discriminating means shown in FIG. 12.
Figure 16:
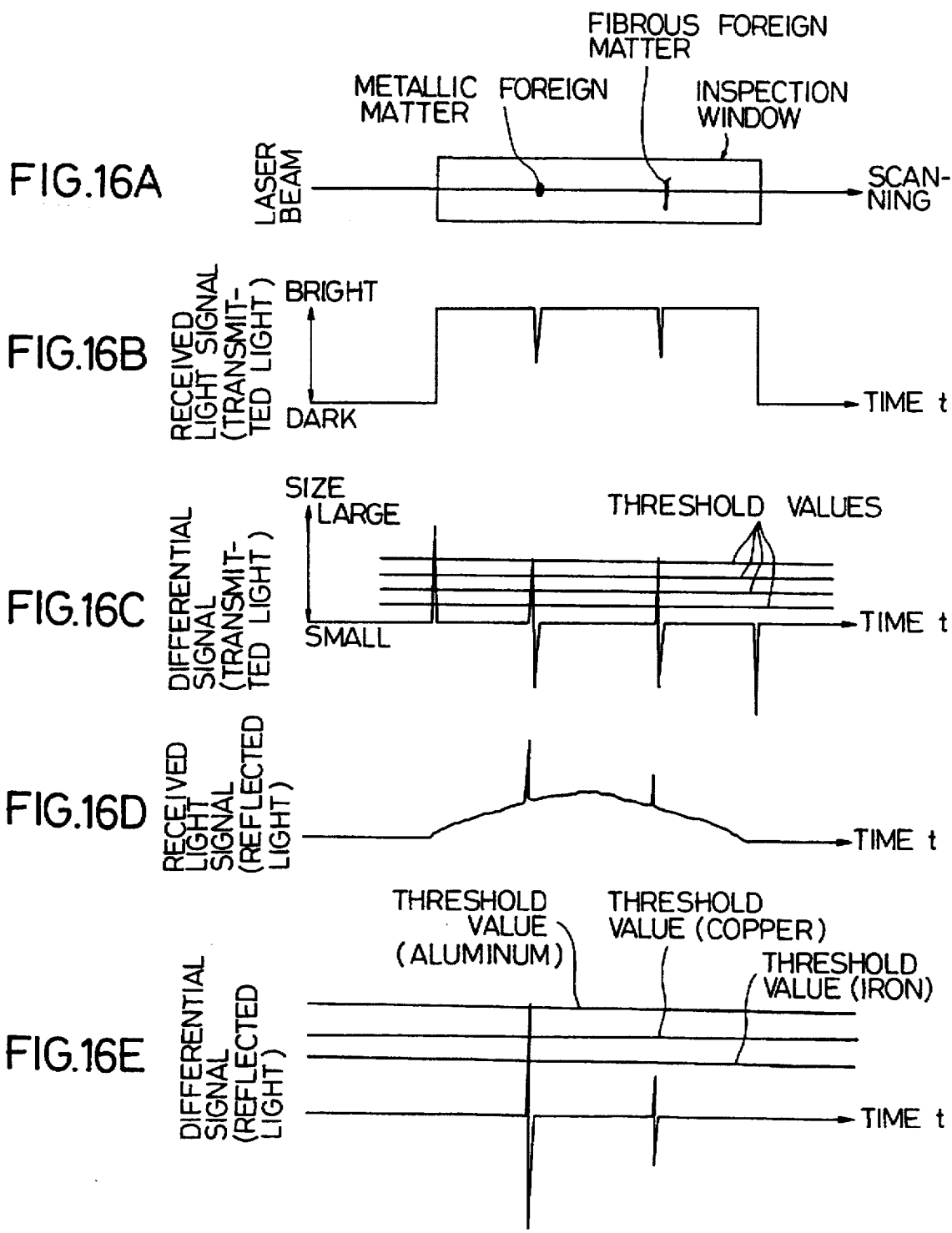
FIGS. 16A to 16E show principal waveforms at various parts of the projecting means, light receiving means, and scattered light receiving means shown in FIG. 12.

As shown in the block diagram of FIG. 15, the scattered light receiving means 91 includes a photomultiplier 93 and a differentiator 94. The discriminating means 92 includes four correction circuits 95a to 95d connected to the differentiator 94, gate circuits 96a to 96d connected to the correction circuits 95a to 95d, respectively, a discriminator 97 connected to the gate circuits 96a to 96d, and detectors 98a1 to 98a4, 98b1 to 98b4, 98c1 to 98c4, and 98d1 to 98d4 provided corresponding to the four gate circuits 96a to 96d and connected to the discriminator 97.

The photomultiplier 93 receives the scattered light beams reflected by a foreign matter, if any, in the plastic flowing through the plastic passage 18, and photoelectrically converts the received light quantity, which varies depending on the intensity of the scattered light beams, into an electrical signal.

The differentiator 94 obtains a differential waveform of the change of the received light quantity.

The following is a description of a case in which an Ar laser with a wavelength of 488 nm is used as the light source according to this embodiment, for example. The reflectances of foreign matters obtained with use of a red laser beam from the Ar laser are about 0.8 for copper, 0.6 for iron, 0.4 for white fibers, and 0.2 for black fibers, provided the reflectance of aluminum is 1. In the case where the foreign matter is metallic, therefore, its reflected light quantity and, hence, the variation of the quantity of light received by the scattered light receiver 90 are larger than in the case of a fibrous foreign matter.

Thus, metallic foreign matters can be distinguished from fibrous ones according to the peak value of the received light signal at the photomultiplier 93. Since the reception level of the scattered light receiver 90 is not uniform throughout the inspection range, however, the respective reception levels of the scattered light beams cannot be simply compared.

According to this embodiment, therefore, threshold values corresponding individually to metallic and fibrous foreign matters are set for the peak value of a differential signal obtained by differentiating the received light quantity. Thus, the kinds of detected foreign matters can be discriminated. Since the received light signal at the scattered light receiver 90 also varies depending on the foreign matter size, the threshold values based on the foreign matter size require correction.

If the diameter of a light beam from the laser and the foreign matter size is 100 μm and not larger than 100 μm, respectively, the quantity of light received by the scattered light receiver 90 decreases in proportion to the foreign matter size. If the foreign matter size is larger than 100 μm, on the other hand, the peak value of the received light quantity never changes even though the foreign matter size becomes larger. In this embodiment, therefore, a foreign matter is detected by differentiating the attenuation of light received from the light receiver 80 for light transmission, and the size of the detected foreign matter is discriminated by the peak value of the differential of the attenuation. Since the time t between the start of laser scanning and the detection of the foreign matter is then detected, the position of foreign matter detection in the scanning direction is ascertained by the scanning period.

Since the received light quantity obtained at that time is equivalent to the quantity of scattered light beams from the detected foreign matter, on the other hand, the kind of the foreign matter can be discriminated by detecting the scattered light beams reflected during the time t.

The correction circuits 95a to 95d are arranged corresponding to the detectors 87a to 87d, respectively, and different threshold values corresponding to the kind of the foreign matter to be identified are corrected and set in the correction circuits. The correction circuits 95a to 95d compare the peak value of the differential of an increase of the quantity of received light from the differentiator 94 with these threshold values. More specifically, if the relative reference quantity of light received by the scattered light receiver 90 for an aluminum piece of 100 μm and the peak value of the differential of the increase of the quantity of received light at the differentiator 94 are $V_A$ and B, respectively, in the correction circuit 95d, the threshold value is settled by the reference light quantity $V_A$ in accordance with the reflectance which depends on the kind of the foreign matter, and is compared with the peak value B as follows:

$V_A \times 1 \leq B$ (aluminum),
$V_A \times 0.8 \leq B$ (copper),
$V_A \times 0.6 \leq B$ (iron),
$V_A \times 0.6 > B$ (fiber).

If the foreign matter size is not larger than 100 μm, the threshold value is corrected and set in accordance with the size. If the foreign matter size and correction factor are A and K, respectively, the reference light quantity $V_A$ is given by $V_A = K \times A$.

The correction circuits 95a to 95d compare a threshold value obtained from the reference light quantity $V_A$ and the reflectance with the peak value B. More specifically, the correction circuit 95a is provided for the size of 30 μm, and compares the values as follows:

$K \times 30 \times 1 \leq B$ (aluminum),
$K \times 30 \times 0.8 \leq B$ (copper),
$K \times 30 \times 0.6 \leq B$ (iron),
$K \times 30 \times 0.6 > B$ (fiber).

The correction circuit 95b is provided for the size of 50 μm, and compares the values as follows:

$K \times 50 \times 1 \leq B$ (aluminum),

K×50×0.8≦B (copper),
K×50×0.6≦B (iron),
K×50×0.6>B (fiber).

The correction circuit 95c is provided for the size of 70 µm, and compares the values as follows:

K×70×1≦B (aluminum),
K×70×0.8≦B (copper),
K×70×0.6≦B (iron),
K×70×0.6>B (fiber).

If the peak value B is not smaller than the set threshold value, the correction circuits 95a to 95d deliver the results of comparison (e.g., high-level signals) to the gate circuits 96a to 96d, respectively.

If the results of comparison for aluminum, copper, and iron are lower than the threshold value, the correction circuits of this embodiment deliver no high-level signals. If no high-level signals are outputted, according to this embodiment, the foreign matter can be identified as a fiber by the discriminator 97 even though the result of comparison for the fiber is not outputted.

Although foreign matters are classified into four kinds according to this embodiment, moreover, the present invention is not limited to this arrangement, and may be applied to the detection of any other number of kinds of foreign matters.

The gate circuits 96a to 96d are composed of AND gates 96a1 to 96a3, 96b1 to 96b3, 96c1 to 96c3, and 96d1 to 96d3 which are connected to the correction circuits 95a to 95d, respectively. These AND gates receives detection signals (high-level signals) from their corresponding detectors 87a to 87d, as well as the results of comparison from the correction circuits 95a to 95d. More specifically, the AND gates 96a1, 96b1, 96c1 and 96d1 are supplied with the results of comparison for aluminum, the AND gates 96a2, 96b2, 96c2 and 96d2 with the comparison results for copper, and the AND gates 96a3, 96b3, 96c3 and 96d3 with the comparison results for iron. Thus, the AND gates deliver the comparison results from the correction circuits 95a to 95d to the discriminator 97 in response to detection signals outputted for each foreign matter size during the foreign matter detection. Also, the gate circuits 96a to 96d deliver the detection signals from the detectors 87a to 87d to the discriminator 97.

The discriminator 97 sets the order of priority for the AND gates of the gate circuits 96a to 96d and the detectors 87a to 87d in advance. More specifically, the discriminator 97 gives the highest priority to the group including the AND gates 96a1, 96b1, 96c1 and 96d1, second priority to the group including the AND gates 96a2, 96b2, 96c 2 and 96d2, third priority to the group including the AND gates 96a3, 96b3, 96c3 and 96d3, and lowest priority to the group including the detectors 87a to 87d. On receiving the results of comparison from the AND gates and the detection signals from the detectors 87a to 87d, the discriminator 97 discriminates the comparison result or signal from the detector of the highest priority based on the set order of priority, and delivers only the discriminated comparison result or signal to the detectors 98a1 to 98a4, 98b1 to 98b4, 98c1 to 98c4, or 98d1 to 98d4 which correspond to the AND gate and detector concerned.

Based on the result of comparison or signal received from the discriminator 97, the detectors 98a1 to 98a4, 98b1 to 98b4, 98c1 to 98c4, and 98d1 to 98d4 output detection signals, and give an alarm indicative of the kind of the foreign matter concerned or display the foreign matter kind, for example.

Referring now to the waveforms of FIGS. 16A to 16E, the operation of the foreign matter detecting apparatus shown in FIGS. 12 to 15 is described.

In detecting a foreign matter, if any, the projector 30 applies the light beam 34 with a convergence diameter of 100 µm to the plastic in the plastic passage 18 through the light transmitting portions 21, as shown in FIG. 16A. An inspection window shown in FIG. 16A corresponds to a region of the plastic passage 18 to be scanned with a light beam, and the scanning direction is represented as a transverse direction compared with the scanning time.

A transmitted light beam is received by the photomultiplier 83 of the light receiver 80, and is photoelectrically converted into a voltage signal (received light signal) which corresponds to the light intensity (see FIG. 16B). Then, the differentiator 84 obtains a differential waveform of the change of the received light quantity in accordance with the received light signal, and delivers a differential signal composed of the differential waveform to the comparators 85a to 85d (see FIG. 16C).

Then, the peak value of the differential signal is applied to the comparators 85a to 85d, whereupon it is compared with the four preset threshold values. In the light receiver 80, the lowest of the four threshold values shown in FIG. 16C is set in the comparator 85a, the second lowest in the comparator 85b, the third lowest in the comparator 85c, and the highest in the comparator 85d.

If the foreign matter has a size not smaller than 30 µm, the comparison result from the comparator 85a is delivered to the discriminator 86. If the foreign matter has a size not smaller than 50 µm, the comparison results from the comparators 85a and 85b are delivered to the discriminator 86. If the foreign matter has a size not smaller than 70 µm, the comparison results from the comparators 85a to 85c are delivered to the discriminator 86. If the foreign matter has a size not smaller than 100 µm, the comparison results from the comparators 85a to 85d are delivered to the discriminator 86.

On receiving the results of comparison from the four comparators 85a to 85d, the discriminator 86 discriminates the comparison result from the comparator of the highest priority based on the set order of priority, and delivers only the discriminated comparison result to the detector which corresponds to the comparator concerned.

On receiving the comparison result, one of the detectors 87a to 87d outputs a detection signal, and gives an alarm indicative of the foreign matter size, or displays the foreign matter size concerned. At the same time, the one detector delivers the detection signal to the corresponding gate circuits 96a to 96d.

If any foreign matter exists in the plastic in the plastic passage 18 when a light beam is applied, on the other hand, scattered light is produced by reflection by the foreign matter. The scattered light is received by the photomultiplier 93 of the scattered light receiver 90, and is photoelectrically converted into a voltage signal (received light signal) which corresponds to the light intensity (see FIG. 16D). Then, the differentiator 94 obtains a differential waveform of the change of the received light quantity in accordance with the received light signal, and delivers a differential signal composed of the differential waveform to the correction circuits 95a to 95d (see FIG. 16E).

Then, the peak value of the differential signal is applied to the correction circuits 95a to 95d, whereupon it is compared with the preset threshold values for the individual circuits 95a to 95d. In the light receiver 90, the lowest of the three threshold values shown in FIG. 16E is set to determine whether or not the foreign matter is iron, the medium threshold value is set to determined whether or not the foreign matter is copper, and the highest threshold value is set to determined whether or not the foreign matter is aluminum. These three threshold values are corrected for each of the correction circuits 95a to 95d, and the levels of the individual threshold values vary depending on the foreign matter size even though foreign matters of the same kind are detected.

If the foreign matter is iron, the comparison results (high-level signals) from the correction circuits are delivered to the AND gates 96a3, 96b3, 96c3 and 96d3 of the gate circuits 96a to 96d. If the foreign matter is copper, the comparison results are delivered to the AND gates 96a2 and 96a3, 96b2 and 96b3, 96c2 and 96c3, and 96d2 and 96d3. If the foreign matter is aluminum, the comparison results are delivered to all the AND gates. If the foreign matter is a fiber, moreover, no high-level signals are delivered from any of the correction circuits 95a to 95d to the gate circuits 96a to 96d.

If the foreign matter has a size not smaller than 30 µm, the comparison result and detection signal from the gate circuit 96a are delivered to the discriminator 97. If the foreign matter has a size not smaller than 50 µm, the comparison result and detection signal from the gate circuit 96b are delivered to the discriminator 97. If the foreign matter has a size not smaller than 70 µm, the comparison result and detection signal from the gate circuit 96c are delivered to the discriminator 97. If the foreign matter has a size not smaller than 100 µm, the comparison result and detection signal from the gate circuit 96d are delivered to the discriminator 97.

On receiving the result of comparison and detection signal from any of the gate circuits 96a to 96d, the discriminator 97 discriminates the comparison result or detection signal from the AND gate of the highest priority based on the set order of priority, and delivers only the discriminated comparison result and detection signal to the detector which corresponds to the gate circuit concerned.

Thus, according to this fifth embodiment, the size of the foreign matter is determined by the change of the received quantity of the transmitted light, the scattered light from the foreign matter is received, and the kind of the foreign matter is discriminated by the change of the received light quantity. In the fifth embodiment, therefore, the presence, size, and kind of a foreign matter, if any, contained in a molten resin extruded from the extruder can be detected accurately.

Although the scattered light beams are received by only one scattered light receiver according to the fifth embodiment, the present invention is not limited to this arrangement, and a plurality of scattered light receivers 90 may be arranged in positions where the scattered light beams can be received. In this case, a value obtained by coupling changes of the quantity of received scattered light may be used for the detection of the kind of foreign matters. Alternatively, the kind of foreign matters may be detected according to the greatest change of the received light quantity.

Although the Ar laser is used as the light source in this embodiment, moreover, the present invention is not limited to this arrangement, and lasers of some other types may be used instead. In this case, the reflectance of the foreign matter with respect to a laser beam from the laser used is previously obtained, and the threshold values of the individual comparators are set in advance. For example, where the He—Ne laser is used as the light source, the threshold value is settled by the reference light quantity $V_A$ in accordance with the reflectance which depends on the kind of the foreign matter, and is compared with the peak value B as follows:

$V_A \times 1 \leq B$ (copper),
$V_A \times 0.8 \leq B$ (aluminum),
$V_A \times 0.6 \leq B$ (iron),
$V_A \times 0.6 > B$ (fiber).

If the foreign matter size is not larger than 100 µm, the threshold value is corrected and set in accordance with the size. Provided the foreign matter size and correction factor are A and K, respectively, the reference light quantity $V_A$ is given by $V_A = K \times A$.

The correction circuits 95a to 95c each compare a threshold value obtained from the reference light quantity $V_A$ and the reflectance with the peak value B. More specifically, the correction circuit 95a compares the values as follows:

$K \times 30 \times 1 \leq B$ (copper),
$K \times 30 \times 0.8 \leq B$ (aluminum),
$K \times 30 \times 0.6 \leq B$ (iron),
$K \times 30 \times 0.6 > B$ (fiber).

The correction circuit 95b compares the values as follows:
$K \times 50 \times 1 \leq B$ (copper),
$K \times 50 \times 0.8 \leq B$ (aluminum),
$K \times 50 \times 0.6 \leq B$ (iron),
$K \times 50 \times 0.6 > B$ (fiber).

The correction circuit 95c compares the values as follows:
$K \times 70 \times 1 \leq B$ (copper),
$K \times 70 \times 0.8 \leq B$ (aluminum),
$K \times 70 \times 0.6 \leq B$ (iron),
$K \times 70 \times 0.6 > B$ (fiber).

Thus, also in this case, the presence, size, and kind of foreign matter in a molten resin can be detected with accuracy.

According to the present invention, furthermore, a plurality of lasers with the same frequency and different convergence diameters may be used as light sources so that the foreign matter size can be discriminated more finely. In this case, however, scattered light receivers must be located in positions where scattered light beams emitted therefrom can be separately received without interfering with one another.

In the foreign matter detecting apparatuses according to the present invention, moreover, satisfactory shading should preferably be ensured in order to detect minute foreign matters with high accuracy.

According to the present invention, furthermore, the detection of the foreign matter kind of rough the reception of the scattered light beams may be combined with the use of a plurality of light beams with different convergence diameters or composite light beam according to the embodiments described above. In this case, the scattered light receiver shown in FIG. 15 may be arranged in various other manners. For example, the scattered light receiver may be designed so that its photomultiplier 93 directly receives the scattered light derived from the plurality of light beams or composite light beam. Alternatively, a filter for selecting a specific waveform, among the waveforms of light beams emitted from several light sources, may be provided in front of the photomultiplier 93 so that scattered light beams with the specific waveform can be received. Alternatively, moreover, filters for waveform selection corresponding to the waveforms of the light beams from the light sources are arranged in front of the photomultiplier 93 so that scattered light beams with the individual waveforms can be received, and that the kind of the foreign matter can be identified synthetically by changes of individual received light quantities. In this case, therefore, the presence, size, length, and kind of the foreign matter can be simultaneously detected with accuracy.

If fibers as foreign matter transmit the light beam therethrough, it may be difficult to discriminate such fibrous foreign matters with the use of the detecting means shown in FIG. 14. To cope with such situations, the present invention provides a foreign matter detecting apparatus shown in FIGS. 17 to 20 which uses scattered light, in addition to transmitted light, for detecting the sizes of foreign matters.

Figure 17:
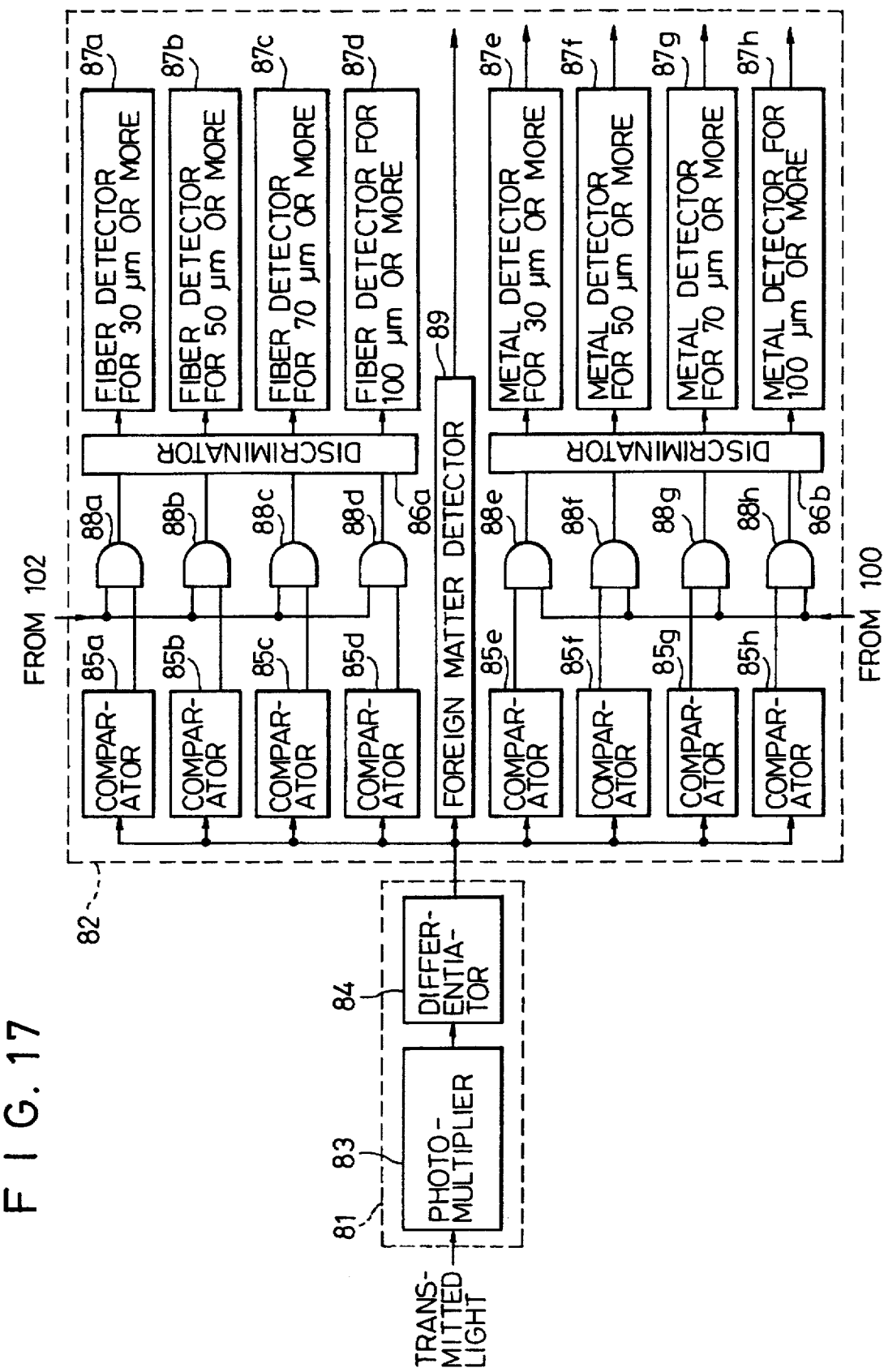
FIG. 17 is a block diagram showing another arrangement for the detecting means in FIG. 14.
Figure 18:
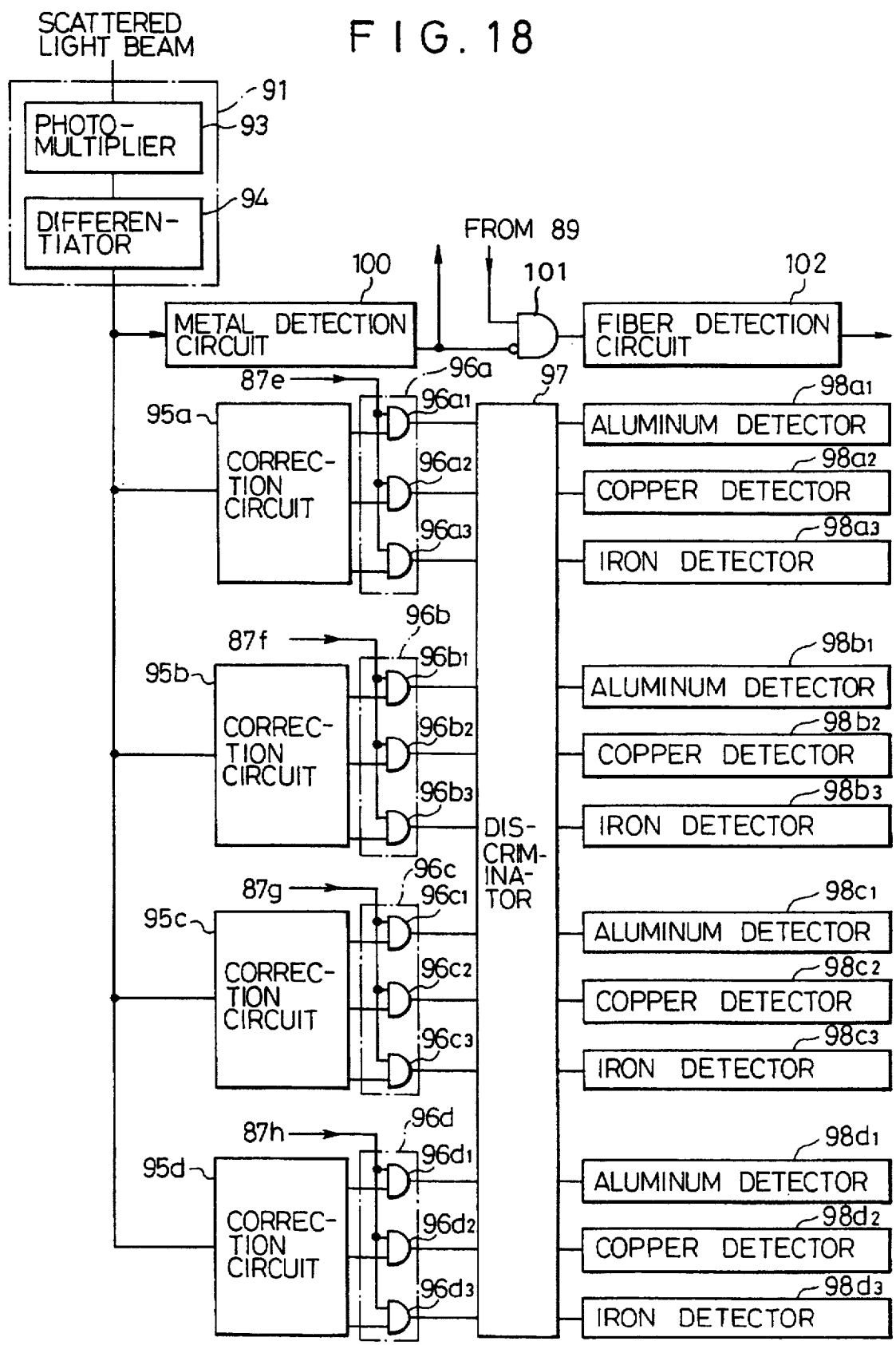
FIG. 18 is a block diagram showing another arrangement for the discriminating means in FIG. 15.

FIG. 17 is a block diagram showing another arrangement for the detecting means in FIG. 14, and FIG. 18 is a block diagram showing another arrangement for the discriminating means in FIG. 15. As shown in FIG. 17, the detecting means 82 comprises eight comparators 85a to 85h connected to the differentiator 84, AND gates 88a to 88h connected to the comparators 85a to 85h, respectively, a discriminator 86 a connected to the AND gates 88a to 88d, a discriminator 86 b connected to the AND gates 88e to 88h, fiber detectors 87a to 87d provided corresponding to the comparators 85a to 85d, respectively, and connected to the discriminator 86 a, metal detectors 87e to 87h provided corresponding to the comparators 85e to 85h, respectively, and connected to the discriminator 86 b, and a foreign matter detector 89 connected to the differentiator 84.

The comparators 85a to 85h are constructed in the same manner as those shown in FIG. 14, and have respective different threshold values preset therein in accordance with the sizes of fiber or metal to be detected. When the peak value of the differential waveform is greater than or equal to the set threshold value, each of the comparators 85a to 85h outputs the result of comparison (e.g., high-level signal) to the corresponding one of the AND gates 88a to 88h.

The AND gates 88a to 88d, which are thus supplied with the comparison results from the respective comparators 85a to 85d, are also supplied with a detection signal from a fiber detection circuit 102, described later. When a fiber is detected by the fiber detection circuit 102, the AND gates 88a to 88d open, thus allowing the comparison results from the respective comparators 85a to 85d to pass therethrough to be supplied to the discriminator 86 a. The AND gates 88e to 88h, which are supplied with the comparison results from the respective comparators 85e to 85h, are also supplied with a detection signal from a metal detection circuit 100, mentioned later. When a metallic matter is detected by the metal detection circuit 100, the AND gates 88e to 88h open, thus allowing the comparison results from the respective comparators 85e to 85h to pass therethrough to be supplied to the discriminator 86 b.

The discriminators 86 a and 86 b are constructed in the same manner as that shown in FIG. 14, and each have a priority order preset therein with respect to the corresponding set of four comparators (85a–85d; 85e–85h). Specifically, the priority order set in the discriminator 86a is in the order of 85d, 85c, 85b and 85a from the highest priority, and the priority order set in the discriminator 86b is in the order of 85h, 85g, 85f and 85e from the highest priority. When the discriminators 86a and 86b are supplied with the comparison results from the corresponding comparators, they discriminate the comparison results from the comparators in the order of priority. The result of comparison thus discriminated is then supplied to one of the detectors 87a–87d and 87e–87h corresponding to the comparator concerned.

In accordance with the result of comparison from the discriminator 86a, the fiber detectors 87a to 87d issue an alarm indicative of the corresponding fiber size or display the fiber size, for example.

The metal detectors 87e to 87h output detection signals based on the comparison results from the discriminator 86ab. The detectors 87e to 87h can issue an alarm indicative of the corresponding metal size, or display the metal size, for example. The detection signals are also supplied to discriminating means of a scattered light receiver shown in FIG. 18.

Figure 19:
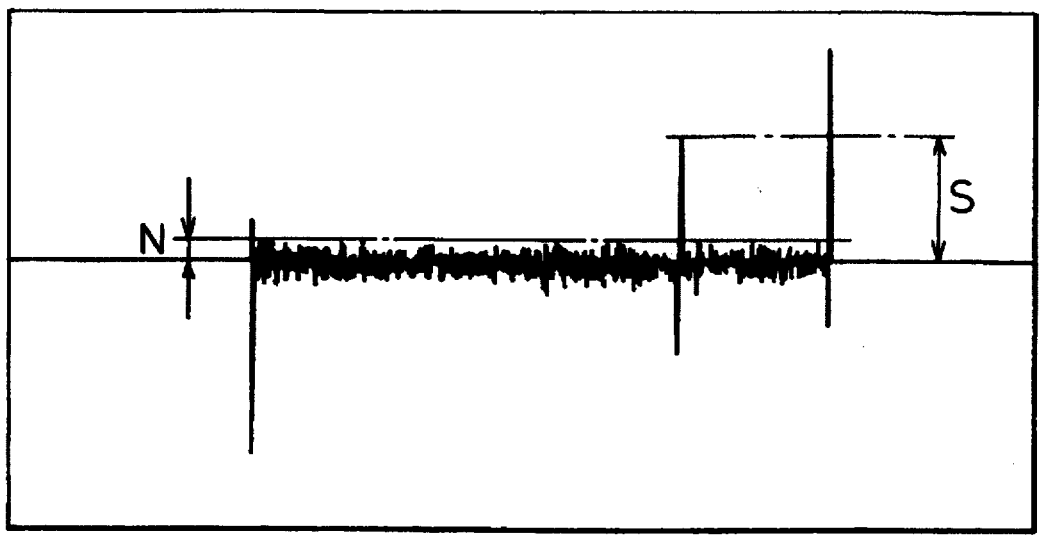
FIG. 19 shows an example of a differential signal waveform actually output from a differentiator shown in FIG. 18.

The foreign matter detector 89 detects the presence of foreign matter based on the differential signal from the differentiator 84. An actual differential signal output from the differentiator 84 contains noise components N, as shown in FIG. 19. In the figure, S represents the peak value of a signal indicative of foreign matter. The threshold value of the foreign matter detector 89 for discriminating the presence of foreign matter is preset to a value 1.5 to 2 times the noise components N, and is compared with the differential signal. Upon detecting a foreign matter, the foreign matter detector 89 outputs a high-level detection signal to an AND gate 101, described later, of the discriminating means shown in FIG. 18.

As shown in FIG. 18, the discriminating means comprises correction circuits 95a to 95d, gate circuits 96a to 96d, a discriminator 97, and detectors 98a1–98a3, 98b1–98b3, 98c1–98c3 and 98d1–98d3, like the discriminating means shown in FIG. 15. The discriminating means further comprises the aforesaid metal detection circuit 100 connected to a differentiator 94, the AND gate 101 connected to the metal detection circuit 100, and the fiber detection circuit 102 connected to the AND gate 101.

The gate circuits 96a to 96d are composed of respective four sets of AND gates 96a1–96a3, 96b1–96b3, 96c1–96c3 and 96d1–96d3 similar to those shown in FIG. 15. Each AND gate is supplied with the comparison result from a corresponding one of the correction circuits 95a to 95d, as well as with the detection signal (high-level signal) from a corresponding one of the detectors 87e to 87h. Accordingly, when a metallic matter is detected, the detection signal, which is generated according to the size of the detected metallic matter, is supplied to the corresponding AND gate, which then opens and allows the comparison result from the corresponding one of the correction circuits 95e to 95h to pass therethrough so as to be input to the discriminator 97.

Upon receiving the comparison results from the AND gates, the discriminator 97 discriminates the comparison results from the gates in accordance with the preset order of priority. The comparison results thus discriminated are supplied to the respective detectors 98a1–98a3, 98b1–98b3, 98c1–98c3 and 98d1–98d3 corresponding to the AND gates.

The detectors can issue an alarm indicative of the corresponding kind of metal or display the kind of metal, for example.

Figure 20:
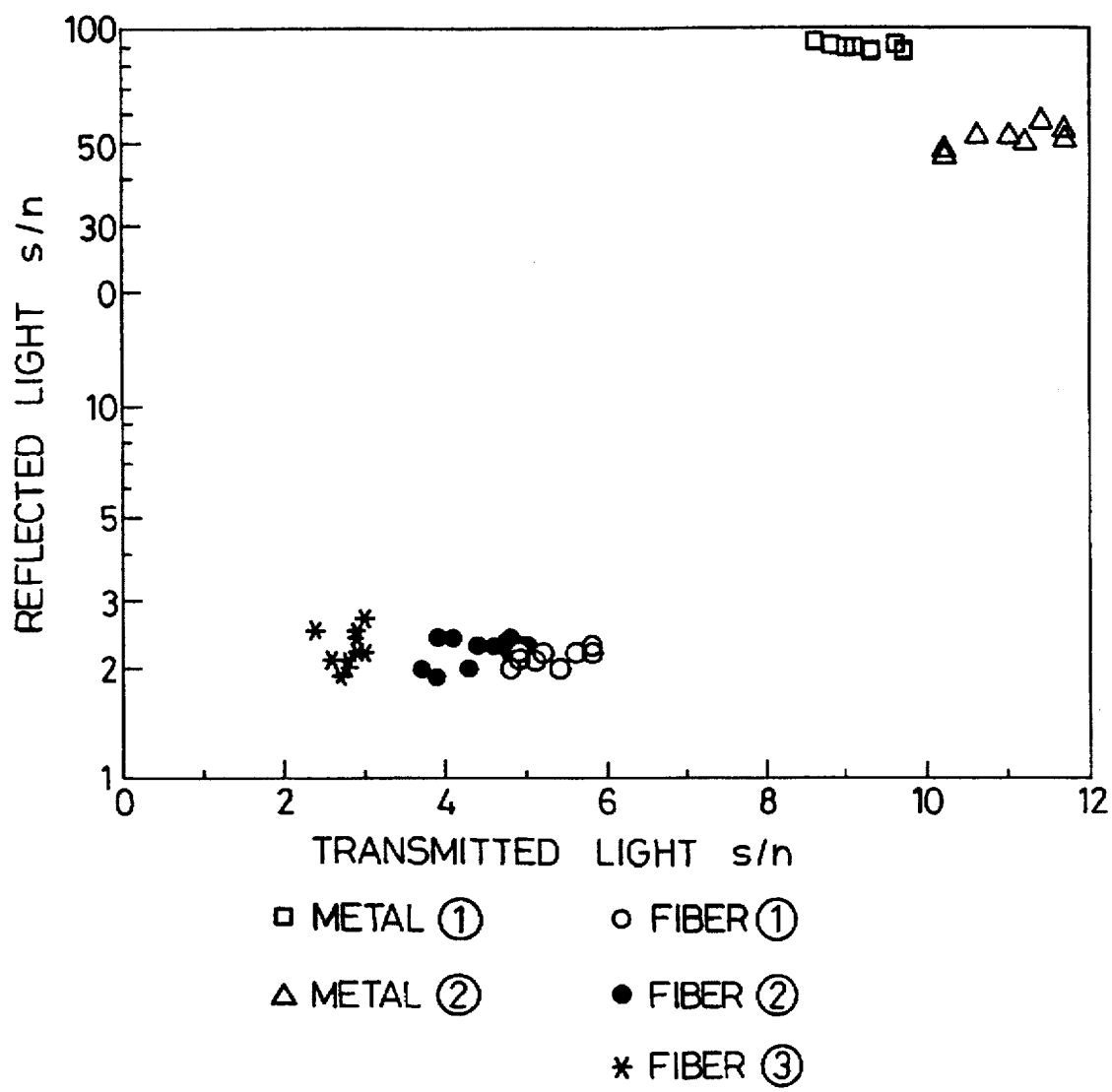
FIG. 20 shows the relationship between the S/N ratio of emitted light and the S/N ratio of scattered light from different fibers and metals.

The metal detection circuit 100 determines whether the detected foreign matter is metallic or not, based on the differential signal from the differentiator 94. The differential signal output from the differentiator 94 represents the S/N ratio of scattered light, and there is a large difference of the S/N ratio between light scattered from fiber and that scattered from metal, as shown in FIG. 20. Thus, the threshold value of the metal detection circuit 100 for discriminating metallic foreign matter is set in advance to a value in the range of 10 to 20, and is compared with the differential signal. When a metallic matter is detected, the metal detection circuit 100 outputs a high-level detection signal to each of the AND gate 101 and the AND gates 88e to 88h shown in FIG. 17.

The AND gate 101 is supplied with an inverted level of the detection signal from the metal detection circuit 100, and when a foreign matter is detected by the foreign matter detector 89, the gate 101 opens, thus allowing the detection signal from the metal detection circuit 100 to pass therethrough to be input to the fiber detection circuit 102.

When supplied with a high-level signal from the AND gate 101, the fiber detection circuit 102 determines the presence of a fiber, and outputs a high-level detection signal to each of the AND gates 88a to 88d shown in FIG. 17.

Thus, in this embodiment, not only the foreign matter detection is carried out based on the transmitted light but also the metallic matter detection is carried out based on the scattered light, and in accordance with these detection results, it is determined whether the detected foreign matter is fibrous or not. Accordingly, even a fiber that permits the light beam to transmit therethrough can be easily discriminated.

Figure 21:
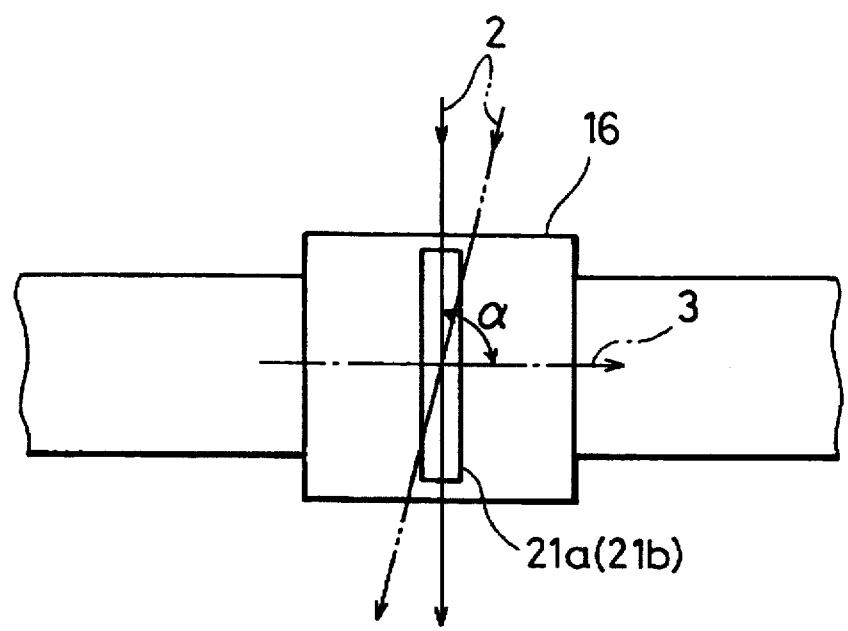
FIG. 21 is a schematic view illustrating a case where the angle between the optical axis of scanning light and the moving direction of fluid has changed.

Preferably, in the foreign matter detecting apparatus of the present invention, the light beam is scanned to be irradiated to the moving fluid in such a manner that the angle α between the scanning axis 2 (solid line) of the light beam transmitted through the light transmitting portion 21a (21b) of the adapter 16 and the moving direction 3 (one-dot-chain line) of the fluid is 90°, as shown in FIG. 21. This angle α has no influence upon the received light signal of the light receiver; therefore, the angle α between the scanning axis 2 (two-dot-chain line) of the light beam and the moving direction 3 of the fluid may not necessarily be 90°. However, with increase in the difference between the angle α and 90°, the width of the adapter 16 (in the moving direction of the fluid) must be increased.

Figure 22:
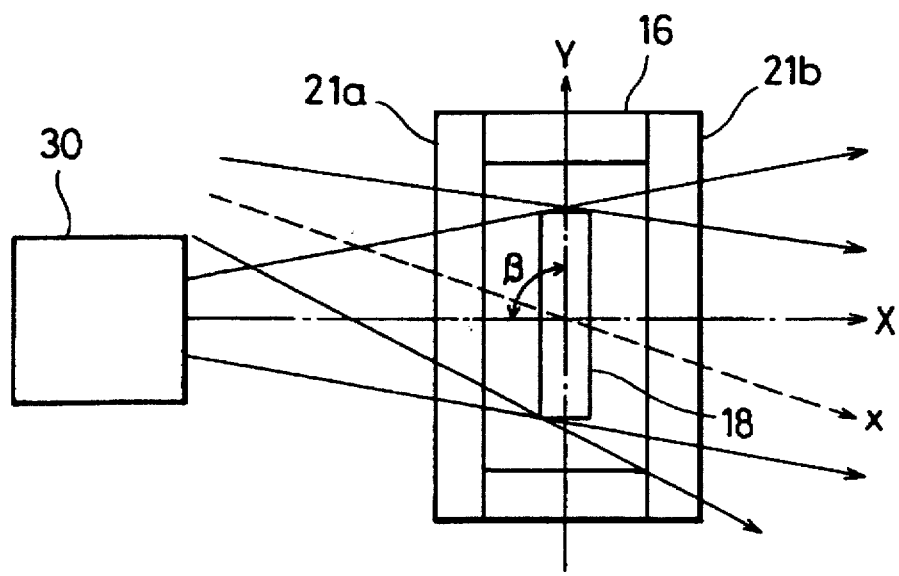
FIG. 22 is a schematic view illustrating a case where the angle between the center axis of scanning light and the longitudinal axis in the section of a passage has changed.
Figure 23:
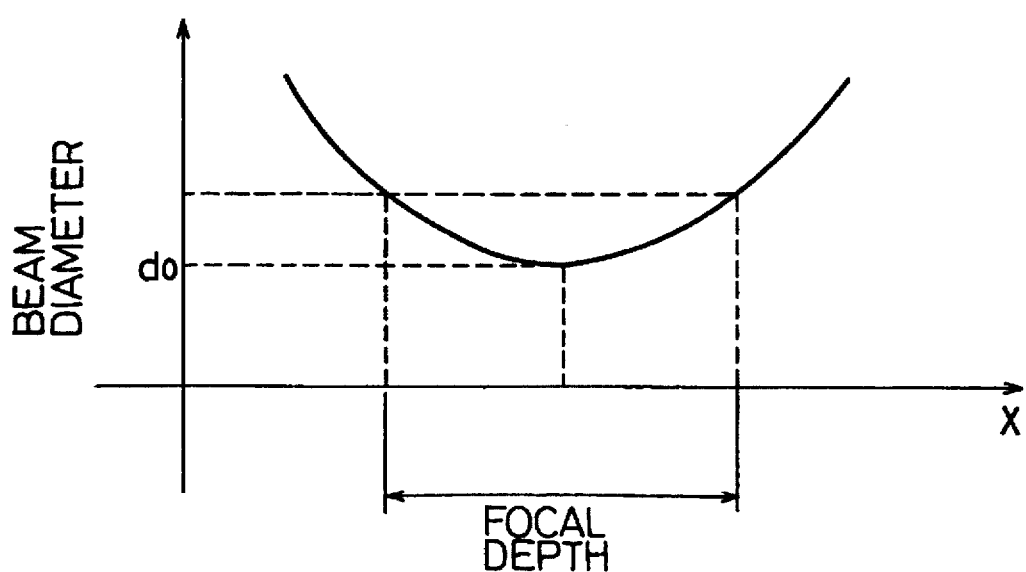
FIG. 23 shows the relationship between the center axis X of scanning light shown in FIG. 22 and beam diameter.
Figure 24:
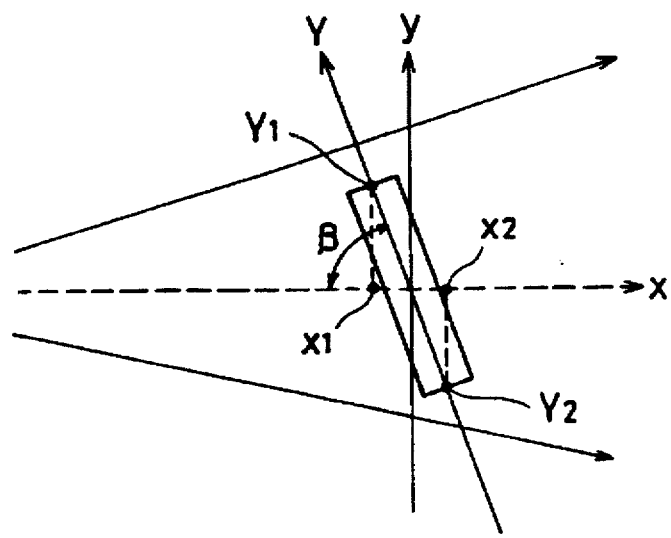
FIG. 24 is a schematic view showing a principal part in FIG. 22.
Figure 25:
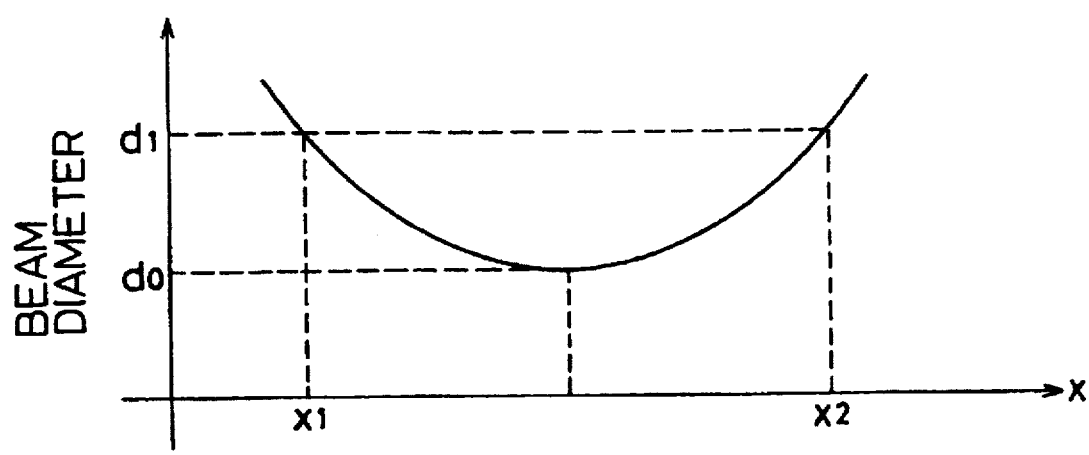
FIG. 25 shows the relationship between the center axis x of scanning light shown in FIG. 22 and beam diameter.

Also, in the foreign matter detecting apparatus of the present invention, the angle β between the center axis X of scanning light (two-dot-chain line) of the light beam transmitted (e.g., from the projector 30) through the light transmitting portion 21a (21b) of the adapter 16 and the longitudinal axis Y in the section of the passage 18 is preferably set to 90°, as shown in FIG. 22. Although the angle β may not necessarily be 90°, the light beam is previously adjusted by the optical system (e.g., condensing lenses 33a, 33b, etc. in FIG. 2) so that the beam diameter takes a minimum value $d_0$ on the center axis Y of the passage 18 within the focal depth (see FIG. 23). Thus, if the angle β becomes greatly deviated from 90° as shown in FIG. 24, the beam diameter is at the minimum $d_0$ on the axis y intersecting the center axis x of scanning light (dashed line) at 90° and takes a greater value $d_1$ at positions $x_1$ and $x_2$ on the scanning axis x corresponding to $Y_1$ and $Y_2$, respectively (see FIG. 25).

The beam diameter is interrelated with the sensitivity of detection; therefore, if the difference ($d_1-d_0$) in beam diameter becomes large, the sensitivity is subject to large change, making it impossible to uniformly detect a foreign matter. In this case, therefore, the angle β should preferably be set so that the beam diameter may be within the range of the focal depth of the optical system.

Figure 26:
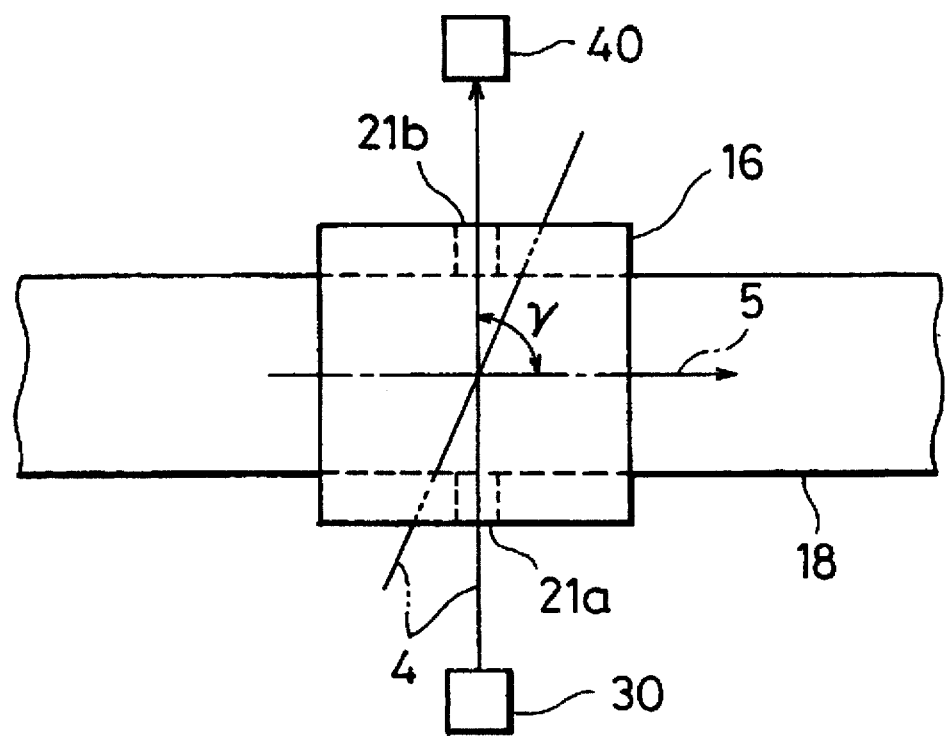
FIG. 26 is a schematic view illustrating a case where the angle between the optical axis and the moving direction of fluid has changed.

Further, in the foreign matter detecting apparatus of the present invention, the light beam is preferably scanned to be irradiated to the moving fluid in such a manner that the angle γ between the optical axis 4 (solid line) of the light beam transmitted (e.g., from the projector 30 to the receiver 40) through the light transmitting portions 21a and 21b of the adapter 16 and the moving direction 5 (one-dot-chain line) of the fluid is 90°, as shown in FIG. 26. The angle γ may not necessarily be 90°, but as the deviation of the angle γ from 90° becomes large, the width of the adapter 16 (in the moving direction of the fluid) must be increased, which complicates the relative positioning of the openings of the light transmitting portions 21a and 21b. Further, if the deviation of the angle γ from 90° is large, the length of the optical axis 4 (two-dot-chain line) passing through the passage 18 prolongs, with the result that the beam diameter increases and the sensitivity is subject to large change, making uniform inspection of foreign matter impossible, as in the case of FIG. 22. Accordingly, in this case, the angle γ is preferably set so that the beam diameter may be within the range of the focal depth of the optical system.

The apparatus of the present invention is used when manufacturing cables such as high-voltage cables, crosslinked polyethylene cables, etc. The invention can also be used when covering an extrusion-molded connecting part for high-voltage cables, for example, with a plastic material.

According to the embodiments described herein, foreign matters to be detected are contained in a plastic. The present invention may, however, be also applied to the detection of foreign matters which exist in, for example, light transmitting rubber or a photoresist material (ultraviolet-curing resin) for semiconductors.

Furthermore, the present invention is not limited to the inspection of resins, and may be also applied to the detection of foreign matters in transparent or translucent fluids or liquids, such as foodstuffs, beverages, medicines, etc., which may be deteriorated by minute foreign matters. Preferably, in this case, an object of inspection should be run downward as it is inspected for the presence of foreign matters if it is lower in specific gravity than the foreign matters therein so that the foreign matters sink. If the specific gravities of the foreign matters are lower than that of the object of inspection so that they float, on the other hand, the object should preferably be run upward to facilitate the detection of the foreign matters.

We claim:

1. An apparatus for detecting foreign matters in a light-transmitting fluid in motion, which apparatus applies light beams to said fluid and detects a foreign matter involved in said fluid by means of transmitted light beams, comprising:

a plurality of projecting means for scanning said light beams with different convergence diameters in a direction crossing the moving direction of said fluid and applying said light beams to said fluid;

a plurality of light receiving means for receiving said light beams transmitted through said fluid during every scanning cycle, and detecting light reception levels of said light beams; and sensing means for previously setting a plurality light reception levels corresponding to the size of the foreign matter, comparing said plurality of set light reception levels with the levels of reception of said light beams detected by said light receiving means, and detecting the size of the foreign matter involved in said fluid in accordance with the results of the comparison.

2. The apparatus for detecting foreign matters in a light-transmitting fluid in motion according to claim 1, further comprising:

detecting means for detecting a length of the foreign matter in accordance with the detection time for the foreign matter continuously detected by said sensing means.

3. An apparatus for detecting foreign matters in a light-transmitting fluid in motion according to claim 2, wherein said sensing means segments a scanning section for said light beams applied to said fluid, and detects the presence of the foreign matter in said fluid in accordance with the levels of reception of said received light beams with every segmented scanning section, and said detecting means detects the length of the foreign matter in accordance with the detection time for the continuously detected foreign matter.

4. An apparatus for detecting foreign matters in a fluid according to claim 2, which further comprises scattered light receiving means for receiving scattered light beams from said fluid, and a discriminating means for correcting the levels of reception of said scattered light beams in accordance with the size of the foreign matter detected by said sensing means and discriminating the kind of the foreign matter in said fluid in accordance with said corrected levels of reception of the scattered light beams.

5. An apparatus for detecting foreign matters in a light-transmitting fluid in motion according to claim 4, wherein said fluid is made of a moving molten resin extruded from an extruder.

6. An apparatus for detecting foreign matters in a light-transmitting fluid in motion according to claim 4, wherein said fluid is made of a moving insulating molten resin extruded from an extruder and used to cover a high-voltage cable.

7. An apparatus for detecting foreign matters in a light-transmitting fluid in motion according to claim 2, wherein said fluid is made of a moving molten resin extruded from an extruder.

8. An apparatus for detecting foreign matters in a light-transmitting fluid in motion according to claim 2, wherein said fluid is made of a moving insulating molten resin extruded from an extruder and used to cover a high-voltage cable.

9. An apparatus for detecting foreign matters in a light-transmitting fluid in motion according to claim 2, wherein the fluid is made of an insulating molten resin used for covering a crosslinked polyethylene cable.

10. An apparatus for detecting foreign matters in a light-transmitting fluid in motion according to claim 2, wherein the fluid is made of an insulating molten resin used for covering an extrusion-molded connecting part for a high-voltage cable.

11. An apparatus for detecting foreign matters in a light-transmitting fluid in motion according to claim 1, wherein said fluid is made of a moving molten resin extruded from an extruder.

12. An apparatus for detecting foreign matters in a light-transmitting fluid in motion according to claim 1, wherein said fluid is made of a moving insulating molten resin extruded from an extruder and used to cover a high-voltage cable.

13. An apparatus for detecting foreign matters in a light-transmitting fluid in motion according to claim 1, wherein the fluid is made of an insulating molten resin used for covering a crosslinked polyethylene cable.

14. An apparatus for detecting foreign matters in a light-transmitting fluid in motion according to claim 1, wherein the fluid is made of an insulating molten resin used for covering an extrusion-molded connecting part for a high-voltage cable.

15. An apparatus for detecting foreign matters in a light-transmitting fluid in motion, which apparatus applies light beams to said fluid and detects a foreign matter involved in said fluid by means of transmitted light beams, comprising:
projecting means for coupling said light beams with different wavelengths and convergence diameters into a composite light beam, for scanning said composite light beam in a direction crossing the moving direction of said fluid, and for applying said composite light beam to said fluid;
light receiving means for receiving said composite light beam transmitted through said fluid during every scanning cycle;
branching means for branching said received composite light beam into light beams for each said wavelength, and detecting light reception levels of said light beams; and sensing means for previously setting a plurality of light reception levels corresponding to the size of the foreign matter, comparing said plurality of set light reception levels with the levels of reception of said light beams detected by said light receiving means, and detecting the size of the foreign matter in said fluid in accordance with the results of comparison.

16. An apparatus for detecting foreign matters in a light-transmitting fluid in motion according to claim 15, wherein said fluid is made of a moving molten resin extruded from an extruder.

17. An apparatus for detecting foreign matters in a light-transmitting fluid in motion according to claim 15, wherein said fluid is made of a moving insulating molten resin extruded from an extruder and used to cover a high-voltage cable.

18. An apparatus for detecting foreign matters in a light-transmitting fluid in motion according to claim 15, wherein the fluid is made of an insulating molten resin used for covering a crosslinked polyethylene cable.

19. An apparatus for detecting foreign matters in a light-transmitting fluid in motion according to claim 15, wherein the fluid is made of an insulating molten resin used for covering an extrusion-molded connecting part for a high-voltage cable.

20. An apparatus for detecting foreign matters in a light-transmitting fluid in motion, which apparatus applies light beams to said fluid and detects a foreign matter involved in said fluid by means of transmitted light beams, comprising:
a plurality of projecting means for scanning said light beams with different convergence diameters in a direction crossing the moving direction of said fluid and applying said light beams to said fluid;
a plurality of light receiving means for receiving said light beams transmitted through said fluid during every scanning cycle, and detecting light reception levels of said light beams;
sensing means for detecting the size of the foreign matter in said fluid in accordance with the levels of reception of said light beams detected by said light receiving means;
scattered light receiving means for receiving scattered light beams from said fluid; and
discriminating means for correcting the levels of reception of said scattered light beams in accordance with the size of the foreign matter detected by said sensing means and discriminating the kind of the foreign matter in said fluid in accordance with said corrected levels of reception of the scattered light beams.

21. An apparatus for detecting foreign matters in a light-transmitting fluid in motion according to claim 20, wherein said fluid is made of a moving molten resin extruded from an extruder.

22. An apparatus for detecting foreign matters in a light-transmitting fluid in motion according to claim 20, wherein said fluid is made of a moving insulating molten resin extruded from an extruder and used to cover a high-voltage cable.

23. An apparatus for detecting foreign matters in a light-transmitting fluid in motion, which apparatus applies light beams to said fluid and detects a foreign matter involved in said fluid by means of transmitted light beams, comprising:
projecting means for scanning said light beams in a direction crossing the moving direction of said fluid and applying said light beams to said fluid;
light receiving means for receiving said light beams transmitted through said fluid during every scanning cycle, and detecting light reception levels of said light beams;

sensing means for detecting the size of the foreign matter in said fluid in accordance with the levels of reception of said light beams detected by said light receiving means;

scattered light receiving means for receiving scattered light beams from said fluid; and discriminating means for correcting the levels of reception of said scattered light beams in accordance with the size of the foreign matter detected by said sensing means and discriminating the kind of the foreign matter in said fluid in accordance with said corrected levels of reception of the scattered light beams.

24. An apparatus for detecting foreign matters in a light-transmitting fluid in motion according to claim 23, wherein said projecting means includes a laser section for applying a laser beam converged to a predetermined diameter to said fluid.

25. An apparatus for detecting foreign matters in a light-transmitting fluid in motion according to claim 23, wherein said fluid is made of a moving molten resin extruded from an extruder.

26. An apparatus for detecting foreign matters in a light-transmitting fluid in motion according to claim 23, wherein said fluid is made of a moving insulating molten resin extruded from an extruder and used to cover a high-voltage cable.

27. An apparatus for detecting foreign matters in a light-transmitting fluid in motion according to claim 23, wherein the fluid is made of an insulating molten resin used for covering a crosslinked polyethylene cable.

28. An apparatus for detecting foreign matters in a light-transmitting fluid in motion according to claim 23, wherein the fluid is made of an insulating molten resin used for covering an extrusion-molded connecting part for a high-voltage cable.

29. An apparatus for detecting foreign matters in a light-transmitting fluid in motion, which apparatus applies light beams to said fluid and detects a foreign matter involved in said fluid by means of transmitted light beams, comprising:

projecting means for scanning said light beams in a direction crossing the moving direction of said fluid and applying said light beams to said fluid;

light receiving means for receiving the light beams transmitted through said fluid during every scanning cycle, and detecting light reception levels of said light beams;

foreign matter detecting means for detecting the presence of a foreign matter in said fluid, based on the levels of reception of the light beams detected by said light receiving means;

scattered light receiving means for receiving scattered light beams from the fluid;

metal detecting means for determining whether the foreign matter involved in the fluid is metallic or not, in accordance with the levels of reception of the light beams received by said scattered light receiving means;

fiber detecting means for determining whether the foreign matter involved in the fluid is fibrous or not, in accordance with the detection results from said foreign matter detecting means and said metal detecting means;

sensing means for detecting the size of a metallic foreign matter involved in said fluid in accordance with the levels of reception of the light beams received by said light receiving means and the detection result from said metal detecting means; and metal discriminating means for correcting the levels of reception of said scattered light beams in accordance with the size of the metallic foreign matter detected by said sensing means and discriminating the kind of the metallic foreign matter in the fluid in accordance with the corrected levels of reception of the scattered light beams.

30. An apparatus for detecting foreign matters in a light-transmitting fluid in motion according to claim 11, which further comprises a fiber discriminating means for discriminating the kind of a fibrous foreign matter involved in the fluid in accordance with the levels of reception of the light beams received by said light receiving means and the detection result from said fiber detecting means.

31. An apparatus for detecting foreign/matters in a light-transmitting fluid in motion according to claim 29, wherein said projecting means includes a laser section for applying a laser beam converged to a predetermined diameter to said fluid.

32. An apparatus for detecting foreign matters in a light-transmitting fluid in motion according to claim 29, wherein said fluid is made of a moving molten resin extruded from an extruder.

33. An apparatus for detecting foreign matters in a light-transmitting fluid in motion according to claim 29, wherein said fluid is made of a moving insulating molten resin extruded from an extruder and used to cover a high-voltage cable.

34. An apparatus for detecting foreign matters in a light-transmitting fluid in motion according to claim 29, wherein the fluid is made of an insulating molten resin used for covering a crosslinked polyethylene cable.

35. An apparatus for detecting foreign matters in a light-transmitting fluid in motion according to claim 29, wherein the fluid is made of an insulating molten resin used for covering an extrusion-molded connecting part for a high-voltage cable.

36. An apparatus for detecting foreign matters in a light-transmitting fluid in motion, which apparatus applied light beams to said fluid and detects a foreign matter involved in said fluid by means of transmitted light beams, comprising:

a plurality of projecting means for scanning said light beams with difference convergence diameters in a direction crossing the moving direction of said fluid and applying said light beams to said fluid;

a plurality of light receiving means for receiving said light beams transmitted through said fluid during every scanning cycle, and detecting light reception levels of said light beams; and sensing means for detecting the size of the foreign matter in said fluid in accordance with the levels of reception of said light beams detected by said light receiving means;

detecting means for detecting a length of the foreign matter in accordance with the detection time for the foreign matter continuously detected by said sensing means;

scattered light receiving means for receiving scattered light beams from said fluid and discriminating means for correcting the levels of reception of said scattered light beams in accordance with the size of the foreign matter detected by said sensing means and discriminating the kind of the foreign matter in said fluid in accordance with said corrected levels of reception of said scattered light beams.

37. An apparatus for detecting foreign matters in a light-transmitting fluid in motion according to claim 36, wherein said fluid is made of a moving molten resin extruded from an extruder.

38. An apparatus for detecting foreign matters in a light-transmitting fluid in motion according to claim 36, wherein said fluid is made of a moving insulating molten resin extruded from an extruder and used to cover a high-voltage cable.

39. An apparatus for detecting foreign matters in a light-transmitting fluid in motion, which apparatus applies light beams to said fluid and detects a foreign matter involved in said fluid by means of transmitted light beams, comprising:

projecting means for coupling said light beams with different wavelenghts and convergence diameters into a composite light beam, for scanning said composite light beam in a direction crossing the moving direction of said fluid, and for applying said composite light beam to said fluid;

light receiving means for receiving said composite light beam transmitted through said fluid during every scanning cycle;

branching means for branching said received composite light beam into light beams for each said wavelength, and detecting light reception levels of said light beams;

sensing means for detecting the size of the foreign matter in said fluid in accordance with the levels of reception of said received light beams;

scattered light receiving means for receiving scattered light beams from said fluid; and discriminating means for correcting the levels of reception of said scattered light beams in accordance with the size of the foreign matter detected by said sensing means and discriminating the kind of the foreign matter in said fluid in accordance with said corrected levels of reception of the scattered light beams.

40. An apparatus for detecting foreign matters in a light-transmitting fluid in motion according to claim 39, wherein said fluid is made of a moving molten resin extruded from an extruder.

41. An apparatus for detecting foreign matters in a light-transmitting fluid in motion according to claim 39, wherein said fluid is made of a moving insulating molten resin extruded from an extruder and used to cover a high-voltage cable.

* * * * *